United States Patent
Inagaki

(10) Patent No.: US 6,635,161 B2
(45) Date of Patent: *Oct. 21, 2003

(54) NOX SENSOR CONTROL CIRCUIT UNIT AND NOX SENSOR SYSTEM USING THE SAME

(75) Inventor: Hiroshi Inagaki, Komaki (JP)

(73) Assignee: NGK Spark Plug Co., Ltd., Nagoya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/252,814

(22) Filed: Feb. 19, 1999

(65) Prior Publication Data

US 2002/0162743 A1 Nov. 7, 2002

(30) Foreign Application Priority Data

Feb. 20, 1998 (JP) ............................................. 10-55862

(51) Int. Cl.⁷ ............................................. G01N 27/407
(52) U.S. Cl. ..................... 204/425; 204/406; 204/408; 205/781; 73/23.31
(58) Field of Search ............................. 204/425, 426, 204/427, 428, 406, 408; 205/781, 784, 785; 73/23.31

(56) References Cited

U.S. PATENT DOCUMENTS

| | | | |
|---|---|---|---|
| 4,770,760 A | | 9/1988 | Noda et al. |
| 4,875,990 A | * | 10/1989 | Kodachi et al. ............ 204/408 |
| 5,265,458 A | * | 11/1993 | Usami et al. .............. 73/23.32 |
| 5,700,367 A | * | 12/1997 | Yamada et al. ............ 205/785 |
| 6,071,393 A | * | 6/2000 | Oshima et al. ............ 204/425 |
| 6,214,207 B1 | * | 4/2001 | Miyata et al. ............. 205/781 |

FOREIGN PATENT DOCUMENTS

| | | | |
|---|---|---|---|
| EP | 0 120 423 | * | 10/1984 |
| EP | 0 678 740 A | | 10/1995 |
| JP | 4-359144 | | 12/1992 |
| WO | 95/30146 | * | 11/1995 |

OTHER PUBLICATIONS

Strobel et al "Chemical Instrumentation: A Systematic Approach", pp. 385–389, 1989.*

* cited by examiner

Primary Examiner—Nam Nguyen
Assistant Examiner—Kaj K. Olsen
(74) Attorney, Agent, or Firm—Sughrue Mion, PLLC

(57) ABSTRACT

A control circuit unit which enables an existing NOx sensor to serve not only as an NOx sensor but also as an oxygen concentration sensor by attachment to an existing NOx sensor. A control circuit unit 31 is connected to an NOx sensor 1. A first pump element control circuit 56 controls a voltage applied to a first pump element 3 so as to control the partial pressure of oxygen in a first processing chamber 9 such that an output voltage of an oxygen concentration detection element becomes substantially constant. A first pump current is detected using a current detection resistor 101 and is then output via an A/D converter circuit 65. A second pump element control circuit 57 applies a constant voltage to a second pump element 5 in a direction so as to pump out oxygen from a second processing chamber 10. A second pump current is detected using a current detection resistor 107 and is then output via an A/D converter circuit 65. A detection signal indicative of the first pump current is used for determining the oxygen concentration of a measurement gas. The detection signal indicative of the first pump current and a detection signal indicative of the second pump current are used for determining the NOx concentration of the measurement gas.

19 Claims, 22 Drawing Sheets

NOX SENSOR CONTROL CIRCUIT UNIT AND NOX SENSOR SYSTEM USING THE SAME

FIELD OF THE INVENTION

The present invention relates to an NOx sensor control circuit unit and an NOx sensor system including the control circuit unit.

BACKGROUND OF THE INVENTION

NOx-concentration measuring apparatus using an NOx sensor for detecting the concentration of nitrogen oxides (hereinafter called NOx) in exhaust gases from internal combustion engines and the like are disclosed, for example, in European Patent Application Laid-Open No. 0678740A1 and SAE Paper No. 960334, pp. 137–142, 1996. An NOx sensor used in such a conventional NOx-concentration measuring apparatus is composed of oxygen-ion conductive solid electrolyte layers that form a first processing chamber and a second processing chamber. The first processing chamber communicates with the gas to be measured (hereinafter called "a measurement gas") via a first diffusion-controlling passage, and the second processing chamber communicates with the first processing chamber via a second diffusion-controlling passage. The solid electrolyte layer of the first processing chamber is sandwiched between porous electrodes so as to form a first pump element and an oxygen-concentration-measuring cell. The solid electrolyte layer of the second processing chamber is sandwiched between porous electrodes so as to form a second pump element.

In the thus-configured NOx-concentration measuring apparatus, a current is made to flow through the first pump element such that an output voltage from the oxygen-concentration-measuring cell attains a predetermined value, thereby controlling the concentration of oxygen in the first processing chamber to a constant level. At the same time, a constant voltage is applied to the second pump element to thereby pump out oxygen from the second processing chamber. As a result, the NOx concentration of a measurement gas can be obtained from the current flowing through the second pump element.

A measurement gas, e.g., exhaust from an internal combustion engine or the like, contains gas components other than NOx, such as oxygen, carbon monoxide and carbon dioxide. Thus, in the aforementioned NOx-concentration measuring apparatus, first, the oxygen concentration of the first processing chamber is controlled to a very low level by means of the first pump element. Then, in the second processing chamber which receives the measurement gas controlled to a low oxygen concentration, a constant voltage is applied to the second pump element in a direction such that oxygen is pumped out from the second processing chamber. As a result, NOx contained in the measurement gas is decomposed into nitrogen and oxygen by means of the catalyzing function of the porous electrodes of the second pump element, and the thus-generated oxygen is then pumped out from the second processing chamber. Thus, the NOx concentration of the measurement gas can be obtained from the current flowing through the second pump element without influence of other gas components contained in the measurement gas.

In the NOx-concentration measuring apparatus, in order to accurately detect the NOx concentration, the NOx sensor must be heated to a predetermined activation temperature (for example, about 850° C.) so that the cells are activated. Therefore, the apparatus is provided with a heater for heating the NOx sensors.

On the other hand, in a lean burn engine, for example, which is run at a lean air-fuel ratio (namely, a high ratio of air to fuel), the resulting exhaust gas tends to contain a relatively large amount of NOx. Accordingly, in order to suppress NOx emissions, the above-mentioned NOx-concentration measuring apparatus is often used to monitor the state of a reducing catalyst installed in an exhaust line. Specifically, the NOx sensor is installed in an exhaust passage of an internal combustion engine downstream of a reducing catalyst in order to measure the NOx concentration of the exhaust gas. When NOx emissions increase, the air-fuel mixture supplied to the internal combustion engine is temporarily controlled to a rich air-fuel ratio so as to emit unburnt gas from the internal combustion engine. The unburnt gas reacts with NOx accumulated in the catalyst, thereby suppressing NOx emissions.

Since the above-mentioned NOx-concentration measuring apparatus cannot measure the air-fuel ratio of the air-fuel mixture supplied to the internal combustion engine, the realization of the above NOx control requires a separate air-fuel ratio measuring apparatus for obtaining an air-fuel ratio from the oxygen concentration of the exhaust. That is, in order to carry out the above NOx control, air-fuel ratio control must also be carried out simultaneously. To meet this end, both the NOx sensor and an oxygen concentration sensor (a so-called air-fuel ratio sensor) must be provided in the exhaust system of the internal combustion engine.

SUMMARY OF THE INVENTION

In view of the foregoing, an object of the present invention is to provide an NOx sensor control circuit unit which enables an existing NOx sensor to serve not only as an NOx sensor but also as an oxygen concentration sensor by attachment to the existing NOx sensor and which can thus simplify the configuration of a detection system for detecting NOx concentration and oxygen concentration (or air-fuel ratio). It is also an object of the present invention to provide an NOx sensor system including the control circuit unit.

The above objects of the present invention are achieved by providing an NOx sensor control circuit unit (hereinafter also referred to as a control circuit unit) adapted for use by connection to an NOx sensor. The NOx sensor for connection to the control circuit unit of the present invention comprises:

First processing chamber: The first processing chamber is an internal chamber of the NOx sensor and is isolated from the surrounding atmosphere. A measurement gas is introduced into the first processing chamber via a first diffusion-controlling passage.

Second processing chamber: The second processing chamber is an internal chamber of the NOx sensor and is isolated from the surrounding atmosphere. A gas contained in the first processing chamber is introduced into the second processing chamber via a second diffusion-controlling passage.

Oxygen concentration detection element: The oxygen concentration detection element is formed of an oxygen-ion conductive solid electrolyte, sandwiched between porous electrodes, and measures the oxygen concentration of gas in the first processing chamber.

First pump element: The first pump element is formed of an oxygen-ion conductive solid electrolyte sandwiched between porous electrodes, and pumps out oxygen from the first processing chamber.

Second pump element: The second pump element is formed of an oxygen-ion conductive solid electrolyte sandwiched between porous electrodes, and pumps out oxygen from the second processing chamber.

Heating element: The heating element heats the first pump element, the oxygen concentration detection element, and the second pump element.

The control circuit unit of the present invention comprises:

First pump element control circuit: The first pump element control circuit controls voltage applied to the first pump element to thereby control the partial pressure of oxygen in the first processing chamber such that an output voltage from the oxygen concentration detection element becomes substantially constant.

First pump current detection circuit: The first pump current detection circuit detects current flowing through the first pump element (first pump current) and outputs a detection signal indicative of the detected current (hereinafter referred to as a first pump current detection signal).

Second pump element control circuit: The second pump element control circuit applies a constant voltage to the second pump element in a direction so as to pump out oxygen from the second processing chamber.

Second pump current detection circuit: The second pump current detection circuit detects current flowing through the second pump element (second pump current) and outputs a detection signal indicative of the detected current (hereinafter referred to as a second pump current detection signal).

Heating control circuit: The heating control circuit controls heating performed by the heating element.

The first pump current detection signal is used to determine the oxygen concentration of the measurement gas. The first pump current detection signal and the second pump current detection signal are used to determine the NOx concentration of the measurement gas.

An NOx sensor system of the present invention comprises the above NOx sensor and the above control circuit unit connected to the NOx sensor.

According to the above NOx sensor control circuit unit or NOx sensor system, by employing the first pump current detection circuit and the second pump current detection circuit, the first pump current detection signal can be used to determine the oxygen concentration of the measurement gas, and the first pump current detection signal and the second pump current detection signal can be used to determine the NOx concentration of the measurement gas. Accordingly, by connection to an existing NOx sensor, the NOx sensor control circuit unit enables the existing NOx sensor to serve not only as an NOx sensor but also as an oxygen concentration sensor, and thus simplifies the configuration of a detection system for detecting the NOx concentration and the oxygen concentration (air-fuel ratio).

Studies conducted by the inventors of the present invention have revealed the following. Variations in the oxygen concentration of a measurement gas introduced into the first processing chamber influence the NOx concentration dependence of the second pump current. Thus, a conventional method for obtaining the NOx concentration from only the second pump current fails to accurately determine the NOx concentration. By contrast, the NOx sensor control circuit unit or the NOx sensor system of the present invention determines the NOx concentration based on both the detection signal indicative of the first pump current, which reflects the oxygen concentration of the measurement gas, and the second pump current detection signal, thus enabling highly accurate measurement.

In this case, the first pump element control circuit can also be considered to control the voltage applied to the first pump element such that the oxygen concentration of the gas introduced from the first processing chamber to the second processing chamber via the second gas passage becomes substantially constant.

The above control circuit unit may further comprise integration means for integrating the first pump element control circuit, the first pump current detection circuit, the second pump element control circuit, and the second pump current detection circuit. The integration means makes the control circuit unit more compact and facilitates its connection to the NOx sensor.

The above control circuit unit may further comprise a microprocessor which serves at least as heating control instruction means for instructing the heating control circuit to control heating performed by the heating element such that the temperature of the first pump element, that of the oxygen concentration detection element, and that of the second pump element approach a target temperature. Thus, by connecting the control circuit unit to the NOx sensor, the temperature of the elements can be controlled. Furthermore, the control circuit unit including the heating control instruction means can be made more compact.

The above control circuit unit may further comprise an A/D converter circuit for converting into digital signals the first pump current detection signal output from the first pump current detection circuit and the second pump current detection signal output from the second pump current detection circuit. Thus, the control circuit unit can directly output, as needed, the first pump current detection signal and the second pump current detection signal in the form of digital signals for enabling digital processing of the signals by a microprocessor or a like device.

In the case where the control circuit unit further comprises a microprocessor, the microprocessor may serve as oxygen concentration information generation means for generating information regarding the oxygen concentration of the measurement gas based on the first pump current detection signal which has undergone A/D conversion by the A/D converter circuit. The microprocessor may also serve as NOx concentration information generation means for generating information regarding the NOx concentration of the measurement gas based on the first pump current detection signal and the second pump current detection signal which have undergone A/D conversion by the A/D converter circuit. Thus, the oxygen concentration information and the NOx concentration information can be obtained from the control circuit unit.

The above control circuit unit may further comprise a D/A converter circuit for converting to an analog signal a digital signal related to at least any of oxygen concentration information, NOx concentration information, air-fuel ratio information generated on the basis of oxygen concentration information, and excess-oxygen ratio information generated on the basis of oxygen concentration information, among digital signals output from the above microprocessor, and for outputting a converted analog signal. Thus, these kinds of information can be made available in the form of analog signals, which can be used more easily as control signals for internal combustion engines such as automobile engines. The control circuit unit may further comprise a display device for displaying at least any of the oxygen concentration of the measurement gas, the NOx concentration of the measurement gas, air-fuel ratio, and excess-oxygen ratio on the basis of the digital signals. Thus, a user can visually grasp such information.

When the above control circuit unit is connected to the NOx sensor further comprising a temperature detection section for detecting the temperature of at least any of the first pump element, the oxygen concentration detection element, the second pump element and the heating element, the above microprocessor may serve as means for performing temperature correction for information regarding the concentration of an object component. The microprocessor generates oxygen concentration information corrected for temperature and NOx concentration information corrected for temperature (oxygen concentration information and NOx concentration information are hereinafter referred to generically as "object component concentration information") on the basis of the temperature detected by the temperature detection section, the first pump current detection signal, and the second pump current detection signal.

Thus, even when the temperature of, for example, the oxygen concentration detection element, temporarily varies due to an abrupt variation of exhaust gas temperature, information regarding the concentration of an object component is generated in the form of concentration information corrected for temperature, thereby maintaining a high degree of detection accuracy. In this case, the temperature of the oxygen concentration detection element may be measured using a separate temperature sensor, such as a thermistor or a thermocouple. However, a solid electrolyte, which constitutes the elements, is characterized in that its internal resistance varies with temperature. Consequently, this feature may be utilized for measuring temperature, thereby yielding an advantage that there is no need for providing a separate temperature sensor, along with simplifying the measuring system. In this case, the oxygen concentration detection element serves as the temperature detection section, and the above control circuit unit may further comprise an internal-resistance measurement control circuit for measuring the internal resistance of the oxygen concentration detection element. In the case where the control circuit unit includes a microprocessor, on the basis of the measured internal resistance, the heating control instruction means implemented by the microprocessor instructs the heating control circuit to control heating performed by the heating element such that the first pump element, the oxygen concentration detection element and the second pump element are heated to a target temperature.

The above internal-resistance measurement control circuit may comprise an internal-resistance detection current application circuit for applying a constant internal-resistance detection current to the oxygen concentration detection element so as to measure the internal resistance of the oxygen concentration detection element. In particular, the internal resistance of the oxygen concentration detection element is simply obtained from the voltage that is developed across the oxygen concentration detection element. In this case, the microprocessor may serve as internal-resistance information detection means for detecting the voltage that is developed across the oxygen concentration detection element when a constant internal-resistance detection current is passed through the oxygen concentration detection element (this voltage is hereinafter referred to as a "resistance detection voltage"), as information regarding the internal resistance of the oxygen concentration detection element.

The above internal-resistance measurement control circuit may further comprise a modification current application circuit for applying a modification current to the oxygen concentration detection element in a direction opposite that of the internal-resistance detection current, after applying the internal-resistance detection current to the oxygen concentration detection element. When the internal-resistance detection current is applied to the oxygen concentration detection element, oxygen is transported within the oxygen concentration detection element in a direction opposite that of the current. This causes a variation in the oxygen concentration as measured at the opposite sides of the oxygen concentration detection element. As a result, when the NOx sensor resumes measuring the object component concentration, the variation of the oxygen concentration may become an error factor and thus impair accuracy in measuring the object component concentration. When the internal resistance of the oxygen concentration detection element is high, oxygen ions have difficulty moving through the oxygen concentration detection element, potentially causing polarization in association with the application of current. Thus, the modification current application means applies a modification current to the oxygen concentration detection element in a direction opposite that of the internal-resistance detection current after the internal-resistance detection current is applied to the oxygen concentration detection element. As a result of applying the modification current, oxygen is transported in reverse direction with respect to the above-mentioned transportation of oxygen. Thus, the varied oxygen concentration approaches a level as measured before the internal resistance is measured, thereby improving accuracy in resumed measurement of the object component concentration as well as canceling the polarized state of the oxygen concentration detection element. In this case, the magnitude and period of application of the modification current may be set such that the application of the modification current causes the reverse transportation of oxygen in an amount substantially equal to that transported when the internal-resistance detection current is applied. For example, a modification current substantially as large as the internal-resistance detection current may be applied for a period of time substantially equal to the period of time that the internal-resistance detection current is applied.

The above control circuit unit or NOx sensor system may further comprise a standard characteristics information storage section for storing information regarding predetermined standard characteristics (hereinafter referred to as "standard characteristics information") representing correlations among the first pump current value, the second pump current value and the NOx concentration of the measurement gas; and a correction data storage element for storing correction data for making the previously measured characteristics of the NOx sensor equal to the standard characteristics. These characteristics represent correlations among the first pump current value, the second pump current value and the NOx concentration of the measurement gas. When the control circuit unit includes a microprocessor, the NOx concentration information generation means implemented by the microprocessor may detect a signal indicative of the first pump current and a signal indicative of the second pump current, may correct the detected values on the basis of correction data, and may generate information regarding the NOx concentration of the measurement gas using standard characteristics information.

Accordingly, even when the NOx concentration of the same measurement gas is measured using different NOx sensors, any of the NOx sensors can provide an accurate measurement. This is because variations in measurement among the sensors are corrected by the correction data peculiar to the individual sensors. There is no need for each NOx sensor to store characteristics which represent correlations among the first pump current value, the second pump current value and the NOx concentration of the measurement gas. That is, storage may be limited to standard characteristics and correction data, so that the storage capacity needed for storing such data is relatively small.

BRIEF DESCRIPTION OF THE DRAWINGS

12 includes is a graph showing an example relationship between an element temperature and the internal resistance of the oxygen concentration detection element.

DESCRIPTION OF SYMBOLS

Figure 1A:
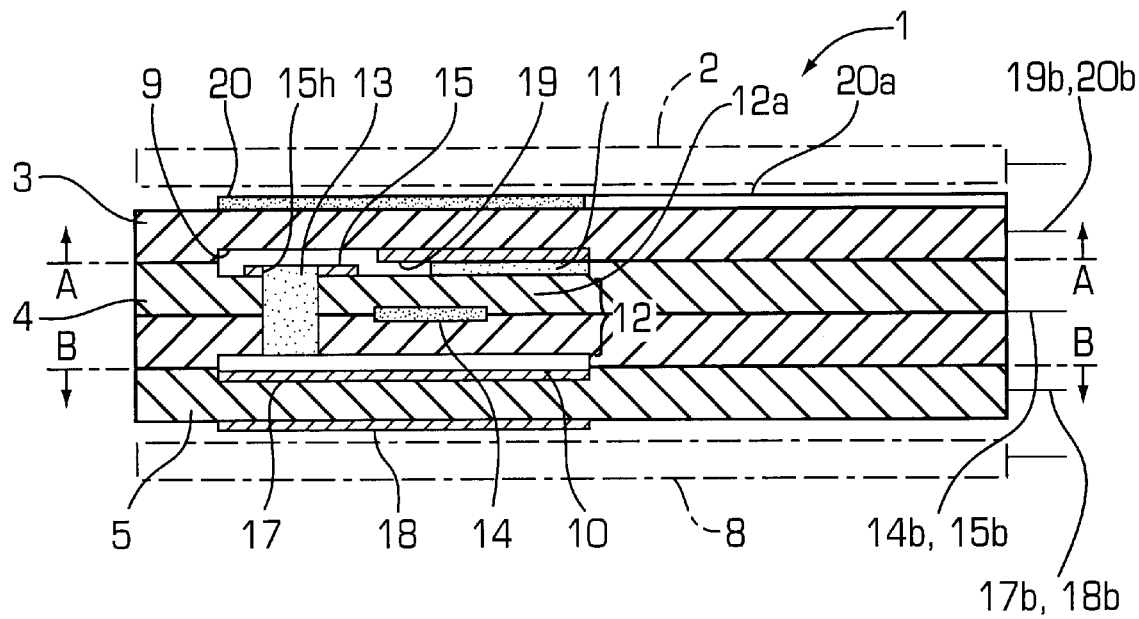
FIG. 1A is a sectional front view showing an example NOx sensor for use in the present invention.

1: nitrogen oxides sensor (NOx sensor)
2: first heater (heating element)
3: first pump element
4: oxygen concentration detection element
5: second pump element
8: second heater (heating element)
9: first processing chamber
10: second processing chamber
11: first gas passage (diffusion-controlling passage)
12: partition wall
13: second gas passage (diffusion-controlling passage)
14: oxygen reference electrode
15, 17, 18, 19, 20: electrodes
30: NOx sensor unit
31: NOx sensor control circuit unit
52: microprocessor
53: CPU (oxygen concentration information generation means,
    NOx concentration information generation means)
54: ROM
55: RAM
56: first pump element control circuit
57: second pump element control circuit
58: reference constant-current power circuit
59: limiter circuit
60: internal-resistance measurement control circuit
61: power circuit
62: pump current control section
63: PID control section
64, 65: A/D converter circuits
66: data storage element
67: D/A converter circuit
68: output circuit
69: display device
72: heater control circuit (heating control circuit)
77, 78: constant-current power circuit

DESCRIPTION OF THE PREFERRED EMBODIMENTS

Embodiments of the present invention will now be described with reference to the drawings.

FIG. 1 shows a nitrogen oxides sensor (hereinafter referred to as an "NOx sensor") 1 according to an embodiment of the present invention. The NOx sensor 1 includes a first heater 2, a first pump element 3, an oxygen concentration detection element 4, a second pump element 5 and a second heater 8. These elements of the NOx sensor 1 are in the shape of an elongated sheet and arranged in layers in this order so as to be integrated into a single unit. A first processing chamber 9 is formed between the first pump element 3 and the oxygen concentration detection element 4. A second processing chamber 10 is formed between the oxygen concentration detection element 4 and the second pump element 5.

The elements 3 to 5 are formed of a solid electrolyte having oxygen-ion conductivity. A typical example of such a solid electrolyte is $ZrO_2$ obtained through solid solution of $Y_2O_3$ or CaO. Another example is a solid solution of $ZrO_2$ and an oxide of an alkaline earth metal or of a rare earth metal. $ZrO_2$ serving as a base material may include $HfO_2$. The present embodiment employs a solid electrolyte ceramic of $ZrO_2$ obtained through solid solution of $Y_2O_3$ or CaO. The first and second heaters 2 and 8, respectively, are known ceramic heaters and are adapted to heat the elements 3 to 5 to a predetermined working temperature of, for example, 750° C. to 850° C., preferably 780° C. to 830° C. (800° C., for example). This heating temperature is set slightly lower than that of conventional NOx sensors in order to improve the durability of the heaters 2 and 8.

An insulating layer (not shown in FIG. 1; an insulating layer 260 is shown in FIG. 3) is interposed between adjacent elements 3 to 5. The insulating layer is primarily formed of $Al_2O_3$. The laminated sensor structure is formed by laminating and subsequent firing of ceramic green sheets (ceramic moldings), which become the elements 3 to 5.

First gas passages 11 are formed at both side wall portions of the first processing chamber 9 so as to establish communication between the first processing chamber 9 and an external atmosphere to be measured. Located on both widthwise sides of the first processing chamber 9 as shown in FIG. 1B, the first gas passages 11 are interposed between and extend along the first pump element 3 and the oxygen concentration detection element 4 in a longitudinal direction of the elements 3 and 4. The first gas passage 11 is formed of a porous ceramic body having communicating pores, which ceramic body is a porous fired body of $Al_2O_3$ or the like. Thus, the first gas passages 11 serve as diffusion-controlling passages for introducing a measurement gas into the first processing chamber 9 from the outside while a constant diffusion resistance is maintained.

A partition wall 12, formed of an oxygen-ion conductive solid electrolyte, is interposed between the first processing chamber 9 and the second processing chamber 10. In other words, the first and second processing chambers 9 and 10, respectively, are arranged with the partition wall 12 interposed therebetween. A second gas passage 13 is formed in the partition wall 12 so as to establish communication between the first processing chamber 9 and the second processing chamber 10. An oxygen reference electrode 14 is embedded in the partition wall 12 at a thickness-wise intermediate portion. As in the case of the first gas passages 11, the second gas passage 13 is formed of a porous ceramic body and serves as a diffusion-controlling passage for introducing a gas into the second processing chamber 10 from the first processing chamber 9 while maintaining a constant diffusion resistance. The diffusion-controlling passages may assume the form of small holes or slits instead of being formed of a porous ceramic body (or a porous metallic body).

A first electrode 15 is formed on the partition wall 12 so as to be exposed to the first processing chamber 9. A main portion of the oxygen concentration detection element 4 includes the first electrode 15, the oxygen reference electrode 14, and a portion 12a of the partition wall 12 interposed between the electrodes 15 and 14. Also, the second pump element 5 has electrodes 17 and 18 formed on opposite surfaces thereof. The first pump element 3 has electrodes 19 and 20 formed on both surfaces thereof. The electrodes 14 and 15 are positioned so as to be shifted from each other in a longitudinal direction of the oxygen concentration detection element 4.

The electrodes 14, 15 and 17 to 20 assume the form of a porous electrode (a porous Pt electrode, for example) and have a reversible catalytic function (oxygen desorption related catalytic function), which catalyzes a desorption reaction for desorbing oxygen molecules therefrom in order to introduce oxygen into solid electrolytes of the elements 3 to 5, and a recombination reaction for recombining with oxygen in order to make the solid electrolytes release oxygen. These porous electrodes are formed in the following manner. In order to improve adhesion between an electrode and a substrate formed of a solid electrolyte ceramic, a metal or alloy powder serving as an electrode material is mixed with an appropriate amount of solid electrolyte ceramic powder similar to that used as the material for the substrate. The resulting mixture is formed into a paste. By using the paste, an electrode pattern is printed on a ceramic green sheet serving as a substrate, followed by firing.

Figure 1B:
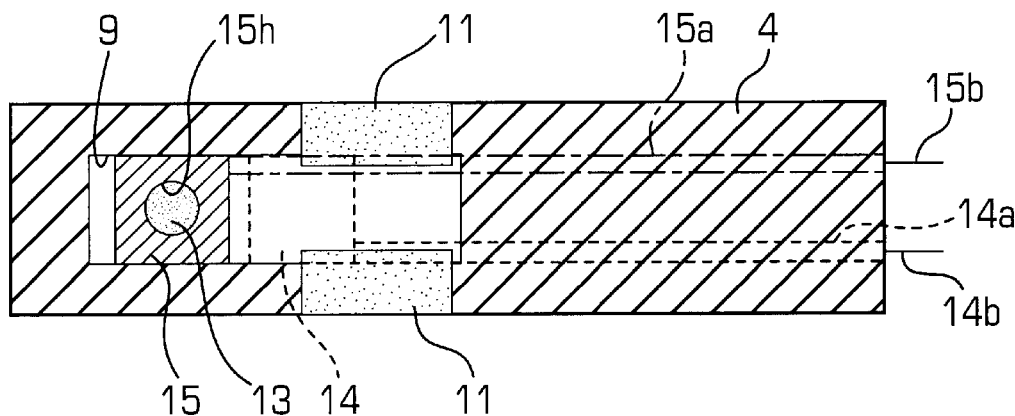
FIG. 1B is a sectional view of the NOx sensor taken along line A—A.
Figure 2:
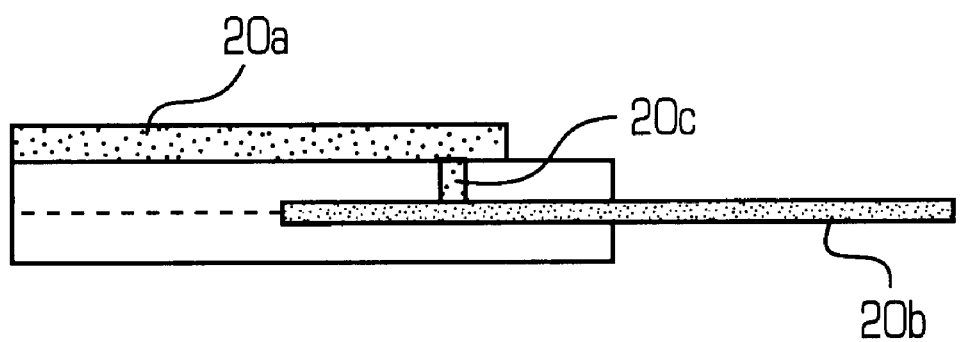
FIG. 2 is a sectional view showing an example connection between an electrode lead and a terminal.

As shown in FIGS. 1A and 1B, electrode leads 14a, 15a and 17a to 20a (FIGS. 1A and 1B show only the leads 14a, 15a and 20a) are integrally formed with the electrodes 14, 15 and 17 to 20, respectively, of the elements 3 to 5, and extend along a longitudinal direction of the elements 3 to 5 toward a sensor end portion. At the sensor end portion, ends of connection terminals 14b, 15b and 17b to 20b are embedded in the elements 3 to 5. As illustrated in FIG. 2, which representatively shows the electrode lead 20a, each connection terminal (20b) is electrically connected to an end portion of each electrode lead (20a) by means of a conductor (20c). The conductor (20c) is formed in the element thickness direction by sintering a metallic paste.

As shown in FIG. 1, the oxygen reference electrode 14 is positioned so as not to interfere with the second gas passage 13. This feature further stabilizes the sensor output indicative of NOx concentration. The first electrode 15 of the oxygen concentration detection element 4 overlaps the second gas passage 13. In order to permit gas flow, a through-hole 15h is formed in the first electrode 15 at a position corresponding to the second gas passage 13.

Figure 3A:
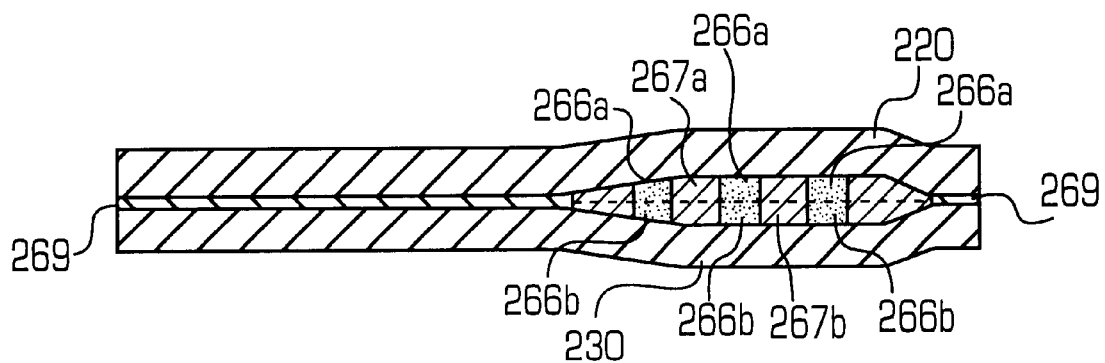
FIGS. 3A and 3B are explanatory views illustrating a process of forming a processing chamber in the NOx sensor of FIG. 1A.
Figure 3B:
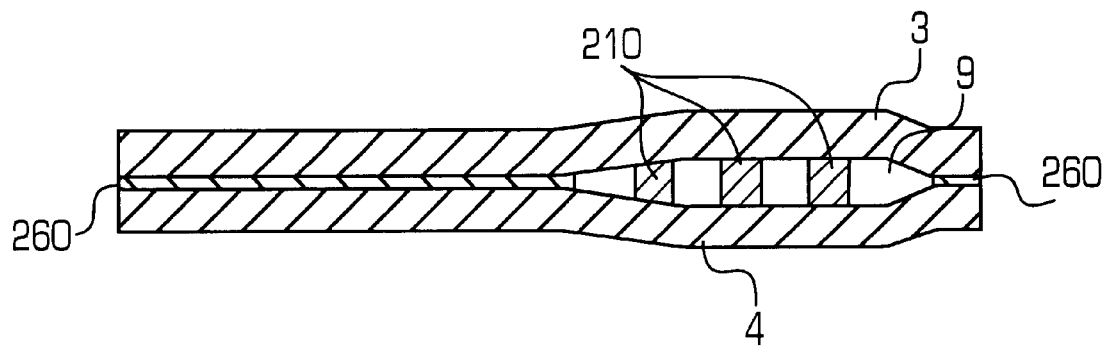

As shown in FIG. 3B, in the first processing chamber 9 and the second processing chamber 10, supports 210 are formed in a scattered or staggered manner to thereby prevent the collapse of the chambers 9 and 10 during firing. The process of forming such a chamber structure will be described, taking the first processing chamber 9 as an example. As shown in FIG. 3A, using a ceramic powder paste (for example, a paste of porous $Al_2O_3$ powder), support patterns 266a are formed on a ceramic green sheet 220 in a region for defining the first processing chamber 9. The ceramic green sheet 220 will be formed into the first pump element 3. Likewise, support patterns 266b are formed on a ceramic green sheet 230 in a region for defining the first processing chamber 9. The ceramic green sheet 230 will be formed into the oxygen concentration detection element 4. The support patterns 266a and 266b will be formed into supports 210. By using a paste material (for example, carbon paste) which will be burned or decomposed during firing, auxiliary support patterns 267a are formed on the ceramic green sheet 220 in a region for defining the first processing chamber 9 so as not to overlap the support patterns 266a. Likewise, auxiliary support patterns 267b are formed on a ceramic green sheet 230 in a region for defining the first processing chamber 9 so as not to overlap the support patterns 266b. Furthermore, using $Al_2O_3$ powder paste, an insulating layer pattern serving as a bonding coat 269 is formed between the ceramic green sheets 220 and 230 in a region other than the region for defining the first processing chamber 9. The thickness of the insulating layer pattern is made smaller than that of the supports 210. Although not shown in FIG. 3, by using a paste of porous $Al_2O_3$ powder, communicating-portion patterns are formed on both sides of the region for defining the first processing chamber 9. Once fired, the communicating-portion patterns will become the first gas passages 11 (FIGS. 1A and 1B).

The thus-prepared assembly of the ceramic green sheets 220 and 230 is subjected to firing. As a result, as shown in FIG. 3B, the support patterns 266a and 266b are united into the supports 210 between the first pump element 3 and the oxygen concentration detection element 4, whereas the auxiliary patterns 267a and 267b disappear. The first processing chamber 9 is formed, while its size is maintained by the supports 210. As shown in FIG. 1B, porous ceramic bodies form the first gas passages 11 on both widthwise sides of the first processing chamber 9. The oxygen concentration detection element 4 and the first pump element 3 are bonded together in a region other than the first processing chamber 9 by means of the bonding coat 269 serving as the insulating layer 260.

Figure 4A:
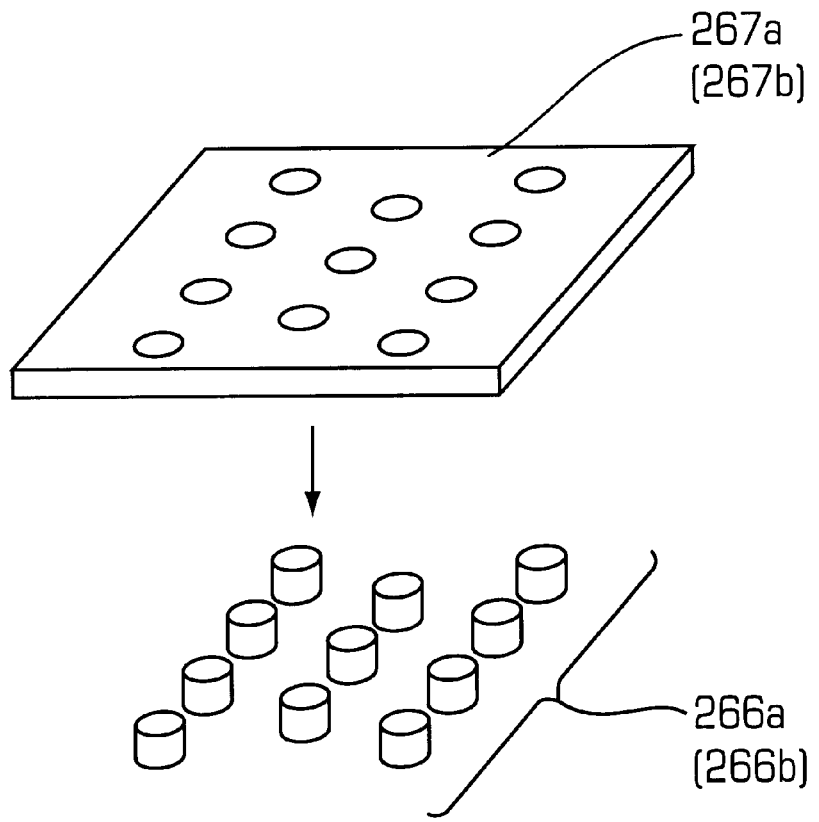
FIGS. 4A, and 4B are explanatory views illustrating the process of forming the processing chamber of the NOx sensor of FIG. 1A.
Figure 4B:
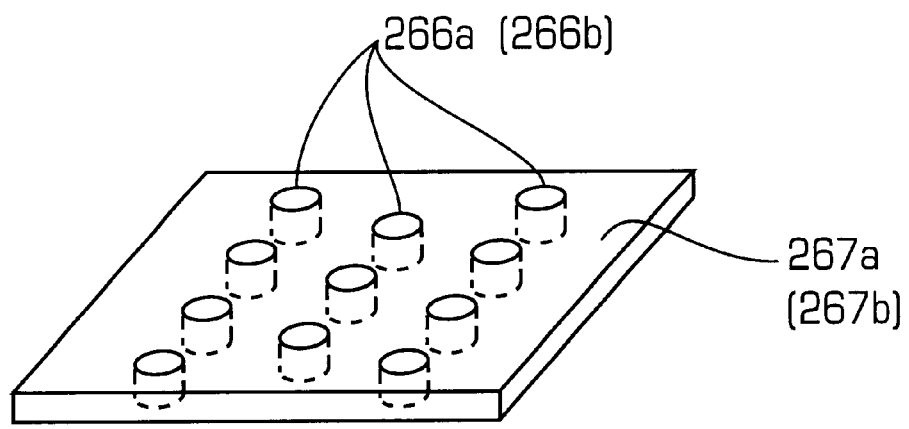

As shown in FIGS. 4A and 4B the support patterns 266a (266b) and the auxiliary support pattern 267a (267b) are complementarily formed to thereby form a substantial plane. When the green sheets 220 and 230 are superposed on each other as shown in FIG. 3A, the reinforcing effect of the auxiliary support patterns 267a and 267b prevents or suppresses the collapse of the support patterns 266a and 266b butting against each other. As exaggeratedly shown in FIG. 3A, even when the bonding coat 269 is made considerably thinner than the total thickness of the support patterns 266a and 266b, the green sheets 220 and 230 can be bonded together by means of the interposed bonding coat 269. Because the green sheets 220 and 230 are flexible, the bonding can be established through slight flexure thereof. Thus, the green sheets 220 and 230 can be smoothly fired into a single unit.

Figure 5:
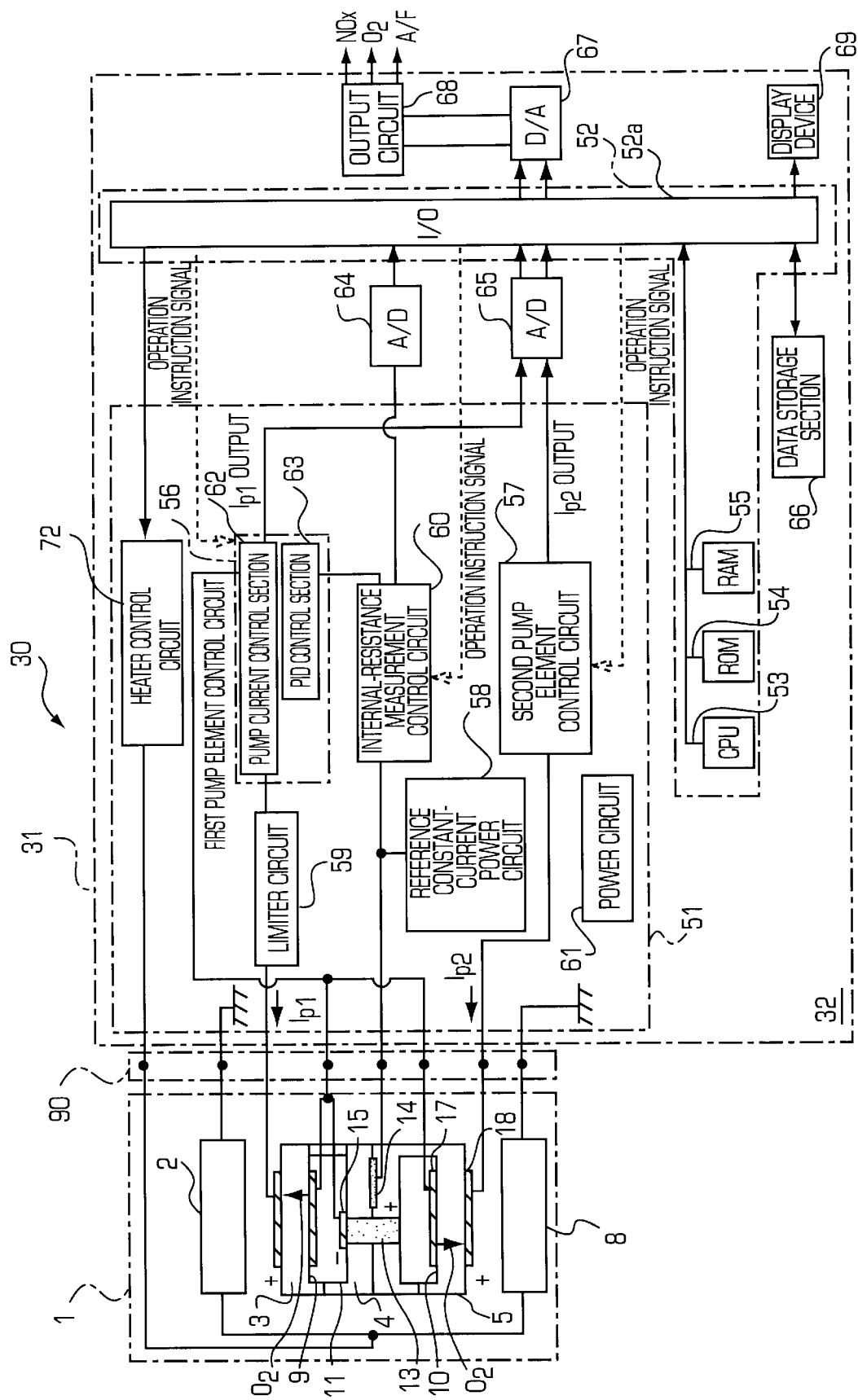
FIG. 5 is an electrical block diagram showing an NOx sensor control circuit unit of the present invention and an NOx sensor system including the NOx sensor control circuit unit.

FIG. 5 shows an example of an electrical block diagram of an NOx sensor system (hereinafter referred to as the "sensor system") of the present invention for use with the NOx sensor 1. Specifically, the sensor system 30 includes the NOx sensor 1 and an NOx sensor control circuit unit (hereinafter referred to as a control circuit unit) 31 according to an embodiment of the present invention and connected to the NOx sensor 1. The control circuit unit 31 includes a microprocessor 52 and a peripheral circuit 51 for connecting the NOx sensor 1 to the microprocessor 52. The microprocessor 52 includes an I/O port 52a serving as an input/output interface, a CPU 53, a RAM 55, a ROM 54, etc. The CPU 53, the RAM 55, the ROM 54 and the like are connected to the I/O port 52a. Using the RAM 55 as a work area and operating according to control programs stored in the ROM 54, the CPU 53 serves as oxygen concentration information generation means and NOx concentration information generation means.

The peripheral circuit 51 includes a first pump element control circuit 56, a second pump element control circuit 57, a reference constant-current power circuit 58, a limiter circuit 59, an internal-resistance measurement control circuit 60, a heater control circuit (heating control circuit) 72, an A/D converter circuit 64 for converting a detection signal output from the internal-resistance measurement control circuit 60 to a digital signal, and an A/D converter circuit 65 for converting detection signals output from the first pump element control circuit 56 and the second pump element control circuit 57 to digital signals. Digital signals output from the A/D converter circuits 64 and 65 are input to the microprocessor 52 through the I/O port 52a.

Also, a data storage element 66 and a D/A converter circuit 67 for converting digital signals output from the microprocessor 52 to analog signals are connected to the I/O port 52a of the microprocessor 52. An output circuit 68 is connected to the D/A converter circuit 67. Based on analog signals received from the D/A converter circuit 67, the output circuit 68 generates and outputs analog signals that reflect information regarding the NOx concentration of a measurement gas, the oxygen (or "$O_2$") concentration of the measurement gas, air-fuel ratio (or "A/F"), and the like. Furthermore, a display device 69 is connected to the I/O port 52a. Based on digital signals output from the microprocessor 52, the display device 69 displays the NOx concentration, the $O_2$ concentration, A/F, and like data in a numerical form, for example.

Figure 6:
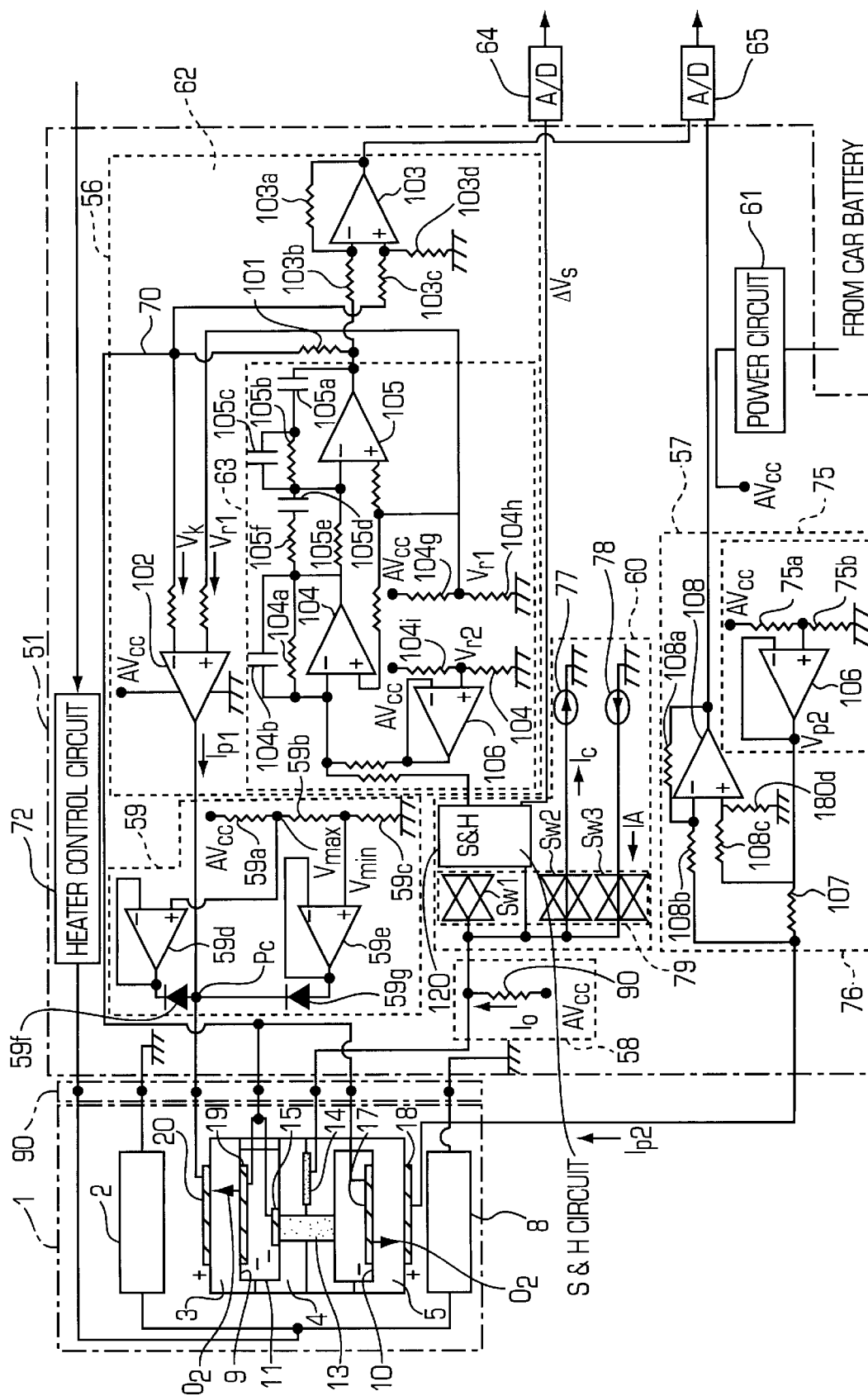
FIG. 6 is a detailed circuit diagram showing a main portion of the NOx sensor control circuit unit.

FIG. 6 shows a detailed block diagram of the peripheral circuit 51. The reference constant-current power circuit 58 is connected to the oxygen concentration detection element 4 on the side of the oxygen reference electrode 14 and applies a supply voltage $AV_{cc}$ to the oxygen concentration detection element 4 via a resistor 90 having a sufficiently large resistance as compared to the internal resistance of the oxygen concentration detection element 4 at sensor working temperatures (about 1000 to 5000 times the internal resistance, for example). As a result, a substantially constant small current $I_0$ is applied to the oxygen concentration detection element in a direction such that oxygen is pumped into the oxygen concentration detection element 4 from the first processing chamber 9 toward the oxygen reference electrode 14, thereby filling the porous oxygen reference electrode 14 with a reference gas having an oxygen concentration of substantially 100%.

The first pump element control circuit 56 includes a pump current controller 62 and a PID controller 63. The input side of the PID controller 63 is connected to the oxygen reference electrode 14 (positive side) of the oxygen concentration detection element 4 via the internal-resistance measurement control circuit 60 and the reference constant-current power circuit 58. The output side of the PID controller 63 is connected to the outer electrode 20 (positive side) of the first pump element 3 via an operational amplifier 102 of the pump current controller 62 and the limiter circuit 59. The electrodes 19 and 15 of the first pump element 3 and the oxygen concentration detection element 4, respectively, which are exposed to the first processing chamber 9, are connected in common to the output side of the PID controller 63 by means of a wiring 70.

The PID controller 63 is primarily composed of two operational amplifiers 104 and 105 and peripheral resistors and capacitors. The first-stage operational amplifier 104, together with a resistor 104a and a capacitor 104b, serves as an inverted amplifier having a low-pass filter function. A reference voltage $V_{r1}$ (2.5 V, for example) is input to the positive side of the operational amplifier 104, and the negative side of the amplifier 104 is connected to the oxygen reference electrode 14. An input voltage to the negative side of the operational amplifier 104 is an output voltage from the oxygen concentration detection element 4. This output voltage is primarily accounted for by an electromotive force that is generated in the oxygen concentration detection element 4 by a concentration cell effect according to the difference between the oxygen concentration of the oxygen reference electrode 14 and that of the first processing chamber 9.

The above-mentioned input to the operational amplifier 104 is biased by a bias voltage $V_{r2}$. The bias voltage $V_{r2}$ is set as a difference $(V_{r1}-V_{emf0})$ obtained by subtracting a target value $V_{emf0}$ of an output voltage $V_{emf}$ of the oxygen concentration detection element 4 from the above-mentioned reference voltage $V_{r1}$. Accordingly, the operational amplifier 104 amplifies the difference "$V_{emf}-V_{emf0}$" and outputs it in an inverted polarity. The reference voltage $V_{r1}$ and the bias voltage $V_{r2}$ are generated by dividing the supply voltage $AV_{cc}$ (in the present embodiment, 8V, for example) by means of resistors 104g and 104h or resistors 104i and 104j.

The second-stage operational amplifier 105, together with peripheral resistors and capacitors 105a to 105f, constitutes a PID operation section and performs a PID operation according to the difference between an input voltage from the operational amplifier 104 and the reference voltage $V_{r1}$. The resistors 105e and 105b form a proportional term; the resistor 105f and the capacitor 105a form an integral term; and the resistor 105e and the capacitor 105d form a differential term. The capacitor 105c allows the PID operation section to function as a lowpass filter.

An output from the PID operation section is input to the operational amplifier 102 adapted for current control and constituting a main portion of the pump current controller 62. The operational amplifier 102 is of a single power source type and varies its output from 0 to a maximum value (in the present embodiment, the supply voltage $AV_{cc}$) according to the difference between an input voltage $V_k$ from the PID operation section and the reference voltage $V_{r1}$, thereby applying a pump voltage (voltage for application of current) $V_p$ to the first pump element 3 in a direction so as to pump out oxygen from the first processing chamber 9. Thus, the current flowing through the first pump element 3, i.e., the first pump current $I_{p1}$', is controlled such that an output voltage from the oxygen concentration detection element 4 is maintained at the above-mentioned target value $V_{emf0}$ using PID control. The output voltage corresponds to the partial pressure of oxygen in the first processing chamber 9. Namely, the output voltage reflects the oxygen concentration of gas introduced into the second processing chamber 10 through the second gas passage 13 on the basis of an electromotive force that is generated in the oxygen concentration detection element 4 by a concentration cell effect.

The limiter circuit 59 limits the maximum value of the pump voltage $V_p$ so that an excessively large pump voltage $V_p$ is not applied to the first pump element 3. The limiter circuit 59 can be realized in various kinds of circuit configurations. In the present embodiment, the limiter circuit 59 employs the following circuit configuration. The limiter circuit 59 is mainly formed of two operational amplifiers 59d and 59e functioning as voltage followers. The operational amplifiers 59d and 59e are connected to a voltage control point $P_C$ via diodes 59f and 59g, respectively, and operate so as to maintain an upper-limit voltage $V_{max}$ (in the present embodiment, 6 V, for example) and a lower-limit voltage $V_{min}$ (in the present embodiment, 2 V, for example), respectively, at their output sides. $V_{max}$ and $V_{min}$ are generated by dividing the supply voltage $AV_{cc}$ by means of resistors 95a to 59c. When a voltage at the control point $P_C$ is about to exceed $V_{max}$, the diode 59f becomes conductive so that the voltage at the point balances the output voltage of the operational amplifier 59d and is thus maintained at $V_{max}$. By contrast, when the voltage at the point is about to drop below $V_{min}$, the diode 59g becomes conductive so that the voltage at the point balances the output voltage of the operational amplifier 59e and is thus maintained at $V_{min}$.

In the pump current controller 62, a current detection resistor 101 is provided on, for example, an output passage of the PID operation section. The resistor 101 is a main element of the first pump current detection circuit. An operational amplifier 103, together with peripheral resistors 103a to 103d, constitutes a differential amplifier. A voltage drop across the resistor 101 is detected as a detection signal indicative of the first pump current $I_{p1}$' (on which a second pump current $I_{p2}$, described later, is superimposed). This voltage signal is converted to a digital signal by the A/D converter circuit 65 and is then input to the microprocessor 52. Alternatively, voltages measured at both ends of the current detection resistor 101 may individually undergo A/D conversion and may then be input to the microprocessor 52, which calculates their difference to thereby determine a relevant current value.

The second pump element control circuit 57 is adapted to apply the second pump voltage $V_{p2}$ to the second pump element 5 in a direction so as to pump out oxygen from the second processing chamber 10, and includes an application voltage generator 75 and a second pump current detection circuit 76. The application voltage generator 75 includes resistors 75a and 75b for generating a predetermined application voltage by dividing the supply voltage $AV_{cc}$ and an operational amplifier 106 functioning as a voltage follower. The output voltage of the operational amplifier 106 is maintained at the pump voltage $V_{p2}$ to be applied to the second pump element 5. The second pump current detection circuit 76 is primarily composed of a current detection resistor 107 provided in, for example, a line for supplying the second pump voltage $V_{p2}$. An operational amplifier 108, together with peripheral resistors 108a to 108d, constitutes a differential amplifier. A voltage drop across the resistor 107 is detected as a detection signal indicative of the second pump current $I_{p2}$. This voltage signal is converted to a digital signal by the A/D converter circuit 65 and is then input to the microprocessor 52 shown in FIG. 5. Alternatively, voltages measured at both ends of the current detection resistor 107 may individually undergo A/D conversion and may then be input to the microprocessor 52.

The target value $V_{emf0}$ of an output voltage of the oxygen concentration detection element 4 is adjusted to the range, for example, of from 300 mV to 500 mV (in the present embodiment, for example, 350 mV). This voltage range corresponds to a partial pressure of oxygen of $10^{-10}$ atm to $10^{-6}$ atm (in the present embodiment, about $10^{-7}$ atm) as calculated in accordance with the Nernst equation. This means that the partial pressure of oxygen in the first processing chamber 9 detected by the oxygen concentration detection element 4, namely, the partial pressure of oxygen in the gas introduced into the second processing chamber 10 through the second gas passage 13, is adjusted to the above-mentioned range.

When the above-mentioned partial pressure of oxygen is less than $10^{-10}$ atm (or when the target output voltage $V_{emf0}$ is not less than 500 mV), NOx in the measurement gas contained in the first processing chamber 9 is excessively decomposed, potentially causing a deterioration of accuracy in detecting NOx. By contrast, when the partial pressure of oxygen is in excess of $10^{-6}$ atm, the concentration of oxygen remaining in the gas introduced into the second processing chamber 10 becomes excessively high, and thus an offset current for the second pump element 5, which will be described later, becomes excessively large, potentially causing a deterioration of accuracy in detecting NOx. According to studies conducted by the present inventors, in view of stability of NOx detection output against variations in sensor temperature and the oxygen concentration of a measurement gas, the partial pressure of oxygen in the first processing chamber 9 is preferably set to a level such that the NOx in the measurement gas introduced into the first processing chamber 9 is decomposed to a certain extent. Accordingly, if the above-mentioned partial pressure of oxygen is in excess of $10^{-6}$ atm, NOx is hardly decomposed, potentially failing to secure stability of NOx detection output.

The internal-resistance measurement control circuit 60 includes a bipolar analog switch circuit 79 composed of, for example, a CMOS-IC. A switch SW1 of the circuit 79 is disposed on, for example, a line extending from the oxygen reference electrode 14 to the first pump element control circuit 56. Furthermore, a sample and hold circuit (hereinafter abbreviated as an S&H circuit) 120 is provided between the analog switch circuit 79 and the first pump element control circuit 56. Constant-current power circuits 77 and 78 providing a current $I_c$ and having different polarities are connected to SW2 and SW3, respectively, of the analog switch circuit 79. An internal-resistance detection signal $\Delta V_S$, described later, output via the S&H circuit 120 is converted to a digital signal by the A/D converter circuit 64 and is then input to the microprocessor 52.

Figure 10:
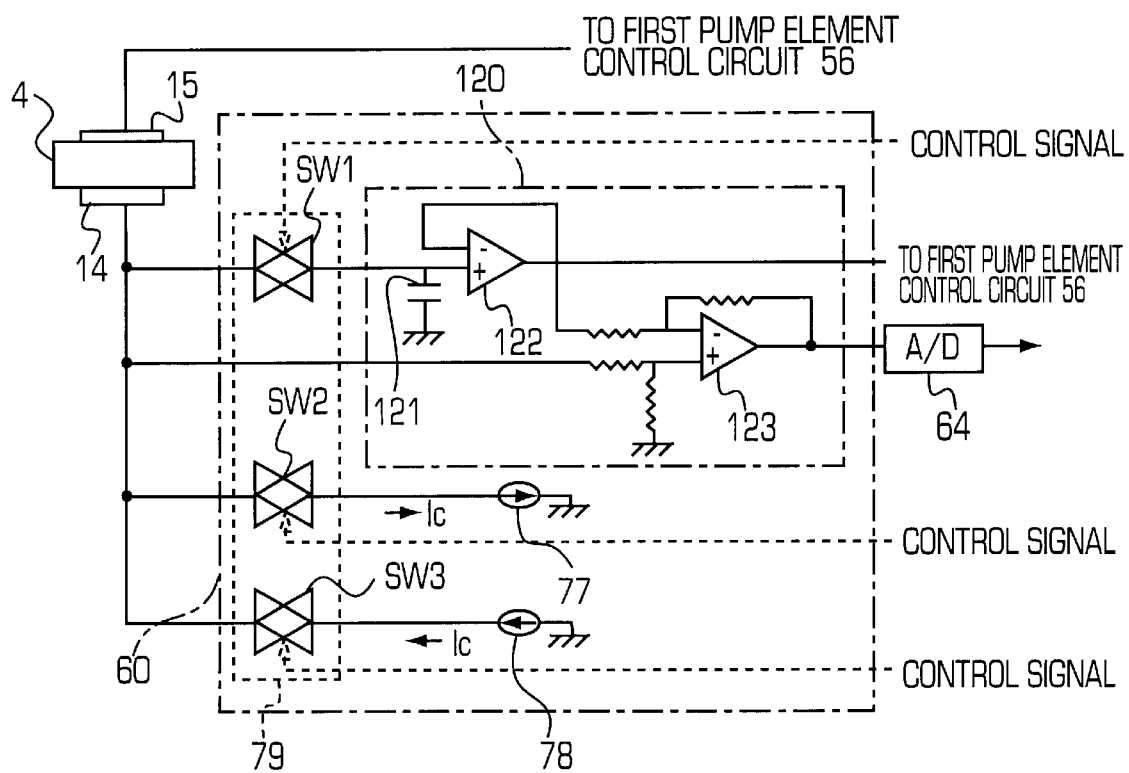
FIG. 10 is a block diagram showing a circuit operation system during measurement of the internal resistance of an oxygen concentration detection element.

Upon receiving a control signal from the microprocessor 52, the first pump current control circuit 56, the second pump current control circuit 57, and the switches SW1 to SW3 of the analog switch circuit 79 turn on and off (see FIG. 10).

Figure 7A:
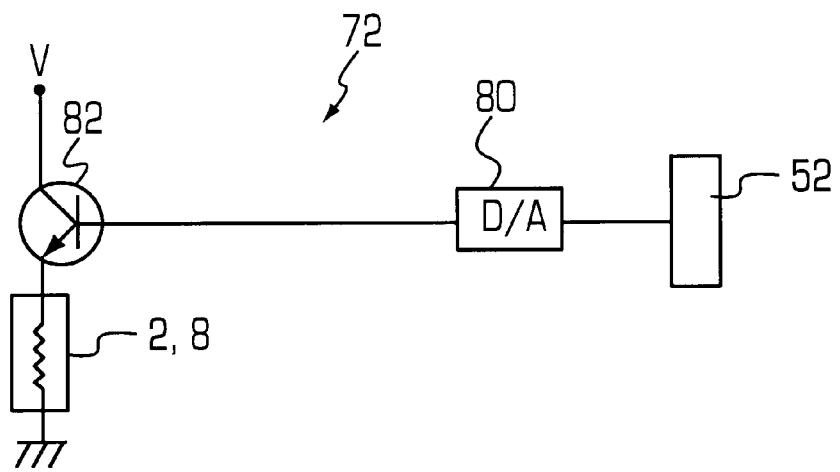
FIGS. 7A and 7B are circuit diagrams showing example heater control circuits.
Figure 7B:
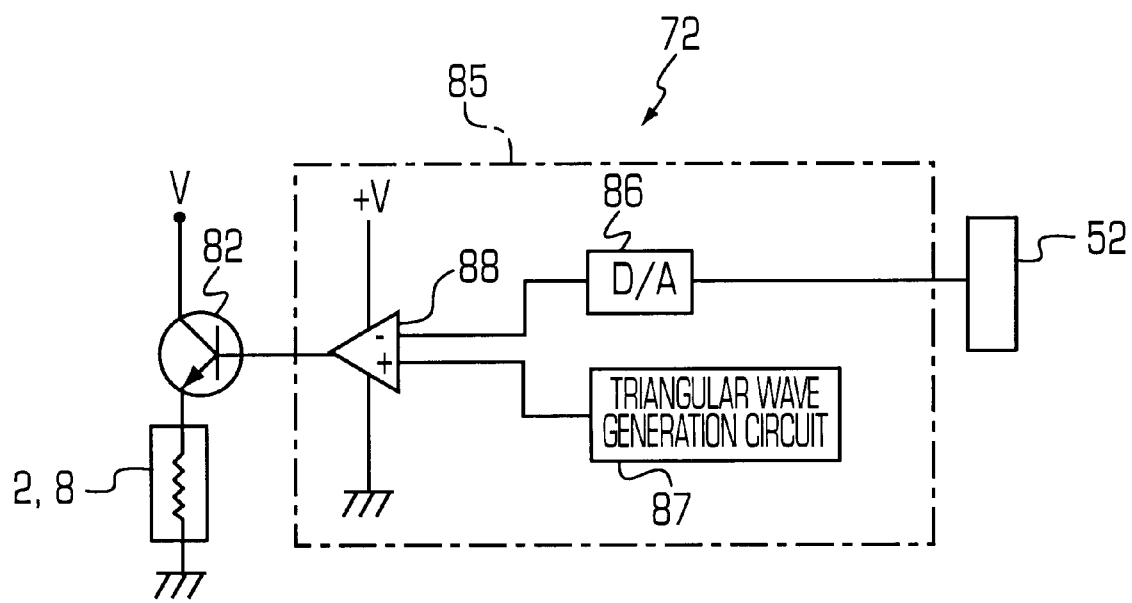

FIGS. 7A and 7B show examples of the heater control circuit 72. The heater control circuit 72 of FIG. 7A includes a D/A converter circuit 80 for converting a heater control value received from the microprocessor 52 to an analog signal; and a transistor 82 connected to the D/A converter circuit 80. The heaters 2 and 8 are connected to the transistor 82. The transistor 82 operates in an active zone and increases current applied to the heaters 2 and 8 according to a received heater control value.

FIG. 7B exemplifies the heater control circuit 72 employing PWM (pulse width modulation) control. The circuit 72 is primarily composed of a PWM control circuit 85, which includes a D/A converter 86 for converting a heater control voltage value received from the microprocessor 52 to an analog signal; a triangular wave (saw tooth wave) generator circuit 87; and an operational amplifier 88 which receives outputs from the D/A converter 86 and the triangular pulse generator circuit 87. The operational amplifier 88 is of a single power source type and serves as a comparator which outputs zero or a predetermined voltage other than zero according to which is larger, the heater control voltage value or the instantaneous value of the input triangular wave. In this case, the duty ratio of the comparator output varies according to the heater control voltage, thereby regulating heating performed by the heaters 2 and 8.

Figure 8:
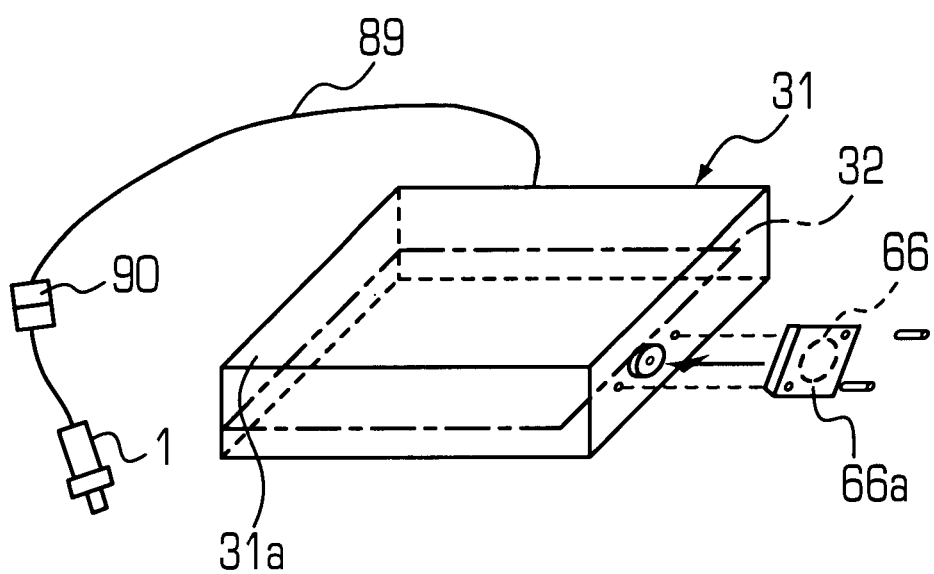
FIG. 8 is a perspective view showing the NOx sensor control circuit unit and NOx sensor system including the NOx sensor control circuit unit.

In FIG. 5, the first pump element control circuit 56, the second pump element control circuit 57, the reference constant-current power circuit 58, the limiter circuit 59, the internal-resistance measurement control circuit 60, the heater control circuit 72, the A/D converter circuits 64 and 65, the microprocessor 52, the D/A converter circuit 67 and the output circuit 68 are mounted on a circuit board 32. As shown in FIG. 8, this board 32 is accommodated within a case 31a, thereby forming the control circuit unit 31. The control circuit unit 31 is removably connected to the NOx sensor 1 via a cable 89 and a connector 90.

Referring back to FIG. 5, the data storage element 66 assumes the form of a semiconductor memory device, which is detachably attached to the microprocessor 52 (hereinafter the element 66 may be referred to as the "semiconductor memory device 66"). In the present embodiment, as shown in FIG. 8, the data storage element 66 assumes the form of an EPROM. The EPROM is implemented by a substantially button-shaped semiconductor memory device (for example, TOUCH MEMORY BUTTON, DS1995, (trade name, product of Dallas Semiconductor Corporation)). The semiconductor memory device 66 has a diameter as small as about 2 cm and is embedded in a substantially rhombic mount 66a (TOUCH MEMORY MOUNT PRODUCT, DS9093x, (trade name, product of Dallas Semiconductor Corporation)). The mount 66a is screwed onto the outer surface of the case 31a.

The operation of the NOx sensor system 30 will next be briefly described. Referring to FIG. 6, the switch SW1 of the analog switch circuit 79 is turned on, and the switches SW2 and SW3 are turned off, thereby activating the first pump element control circuit 56 and the second pump element control circuit 57 (as shown in FIG. 5, the circuits 56 and 57 operate upon reception of an operation instruction signal from the microprocessor 52). A measurement gas is introduced into the first processing chamber 9 via the first gas passage 11. The first pump element 3 causes oxygen to be pumped out from the first processing chamber 9 so as to regulate the oxygen concentration of the chamber 9 such that an output voltage from the oxygen concentration detection element 4 is maintained at the constant target value $V_{emf0}$. At this time, a detection signal indicative of the first pump current $I_{p1}'$ is input to the microprocessor 52 via the A/D converter circuit 64.

The measurement gas having a regulated oxygen concentration is introduced into the second processing chamber 10 via the second gas passage 13. At this time, the second pump current $I_{p2}$ flowing through the second pump element 5 varies with the NOx concentration of the measurement gas. Since the relationship between the second pump current $I_{p2}$ and the NOx concentration varies with the concentration level of oxygen originally in the measurement gas, the NOx concentration can be obtained by determining the oxygen concentration level and the second pump current $I_{p2}$.

In this case, since the first pump current $I_{p1}'$ varies with the oxygen concentration of the measurement gas, the oxygen concentration can be obtained on the basis of the value of the first pump current $I_{p1}'$. However, in the circuit configuration of FIG. 6, as mentioned previously, the first pump current $I_{p1}'$ detected by means of the current detection resistor 101 assumes a value resulting from superimposition of the second pump current $I_{p2}$ on the true current $I_{p1}$ flowing through the first pump element 3. Thus, the oxygen concentration is determined on the basis of ($I_{p1}'-I_{p2}$) (hereinafter, this difference is represented by $I_{p1}$ and is referred to as the "first pump current"). Generally, the current level of $I_{p2}$ is smaller than the current level of $I_{p1}$. Thus, when the influence of the superimposition of $I_{p2}$ is judged negligible, $I_{p1}'$ may be used as an approximate first pump current value.

Figure 9:
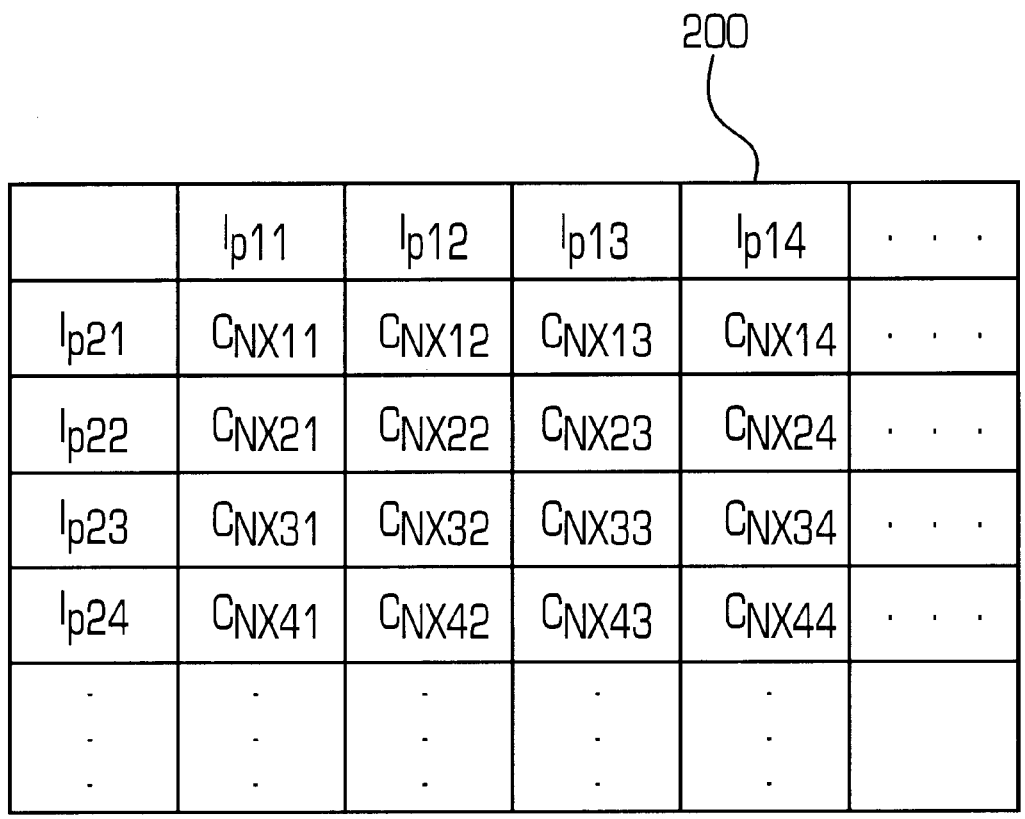
FIG. 9 is a conceptual diagram of a two-dimensional table representing the relationship between $I_{p1}$ and $I_{p2}$ and NOx concentration as stored in a data storage element.

The microprocessor 52 of FIG. 5 determines the oxygen concentration and the NOx concentration in the following procedure. The microprocessor 52 obtains $I_{p1}$ from $I_{p1}'$ and $I_{p2}$ and then determines the oxygen concentration $C_{OX}$ referring to the relationship between $I_{p1}$ and the oxygen concentration $C_{OX}$ (represented in the form of a numeral table or a numeral expression) stored in the data storage element 66. The microprocessor 52 also determines the NOx concentration $C_{NX}$ referring to the relationship among $I_{p1}$, $I_{p2}$ and the NOx concentration $C_{NX}$ (represented in the form of, for example, a two-dimensional numeral table 200 as shown in FIG. 9) stored in the data storage element 66. The two-dimensional numeral table 200 is experimentally prepared for each NOx sensor.

The thus-determined value of $C_{OX}$ or $C_{NX}$ is externally output via the D/A converter circuit 67 and the output circuit

68 in the form of an analog output signal indicative of the oxygen concentration or the NOx concentration, and is sent in the form of digital information to the display device 69 (including a liquid crystal display or a 7-segment LED), which visually displays a concentration value. Notably, the microprocessor 52 may calculate A/F and excess-oxygen concentration based on $I_{p1}$ and may output the calculated values.

In order to maintain appropriate accuracy in detecting the NOx concentration, the temperature of the above-mentioned elements 3 to 5, particularly the temperature of the oxygen concentration detection element 4 for detecting the oxygen concentration of the first processing chamber 9 must be controlled to a constant value. Thus, the current which the heater control circuit 72 applies to the heaters 2 and 8 must be controlled such that the oxygen concentration detection element 4 is heated to a target temperature. In the present embodiment, the microprocessor 52 changes the on and off states of the switches SW1 to SW3 of the analog switch circuit 79 to thereby detect the temperature of the oxygen concentration detection element 4 in the form of the internal resistance $RV_S$, and instructs the heater control circuit 72 to control current applied to the heaters 2 and 8 such that the detected internal resistance $RV_S$ assumes a constant value (i.e., such that the temperature of the oxygen concentration detection element 4 is maintained at the target temperature).

Figure 12:
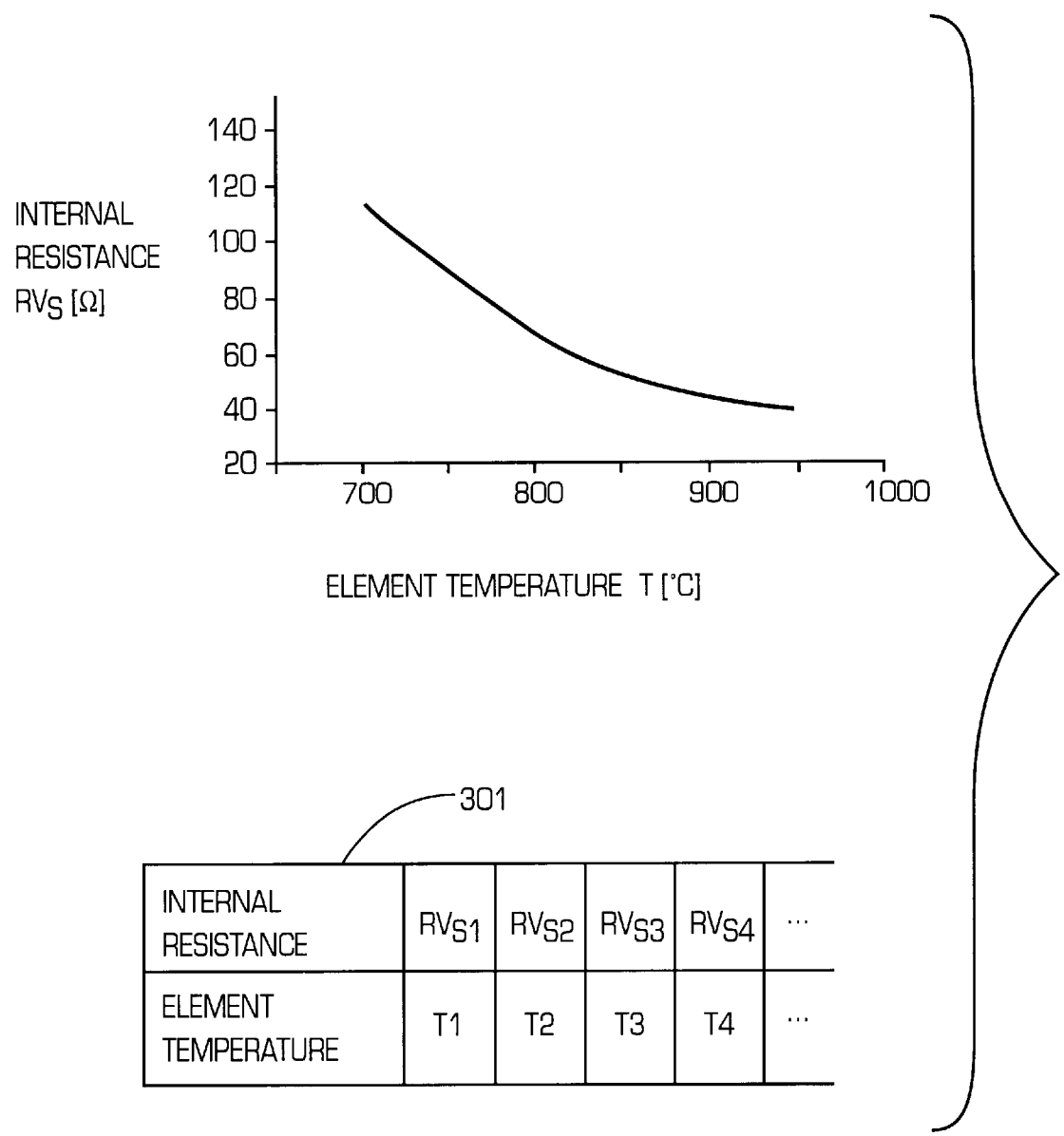
FIG. 12 also includes conceptual diagram of a map showing the relationship between the element temperature and the internal resistance of the oxygen concentration detection element.
Figure 14:
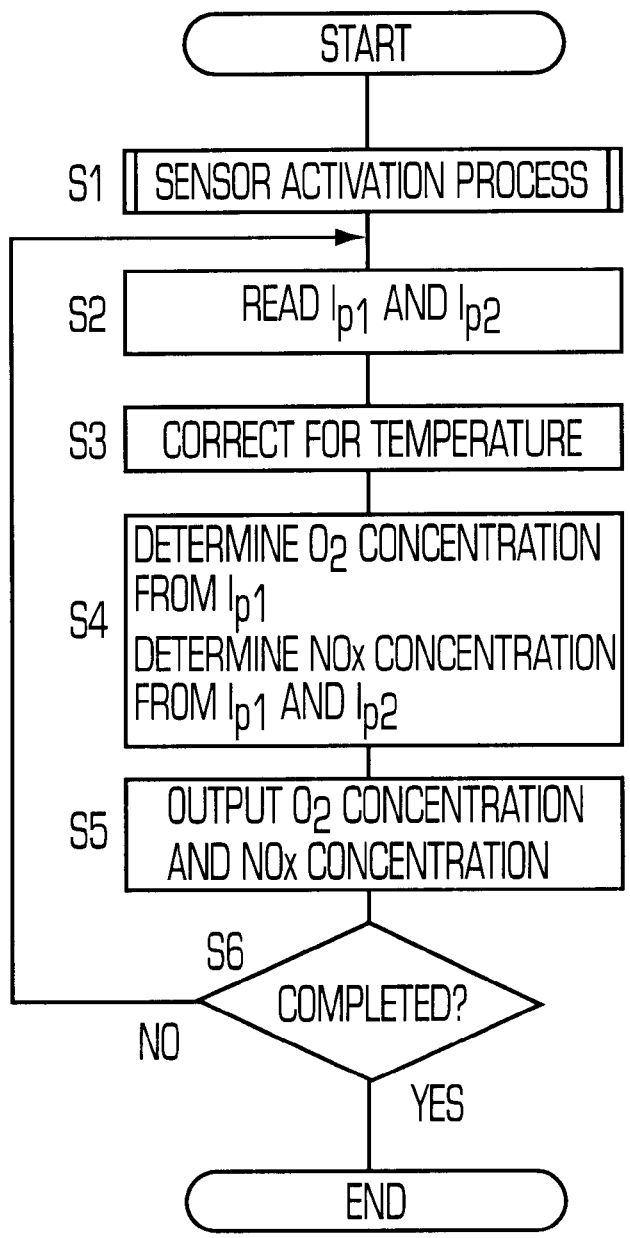
FIG. 14 is a flowchart showing the control steps performed by a microprocessor in the system of FIG. 5.

The temperature control operation will next be described with reference to the flowcharts of FIGS. 14 to 16. In step S1 of FIG. 14, an activation process is performed for the NOx sensor 1. The activation process is intended to apply current to the heaters 2 and 8 so as to heat and stabilize the elements 3 to 5 to a predetermined working temperature. In order to detect the element temperature, the internal resistance of the oxygen concentration detection element 4 is measured, and then the element temperature is determined from the fact that the internal resistance $RV_S$ exhibits a certain temperature dependence as shown in FIG. 12.

Figure 15:
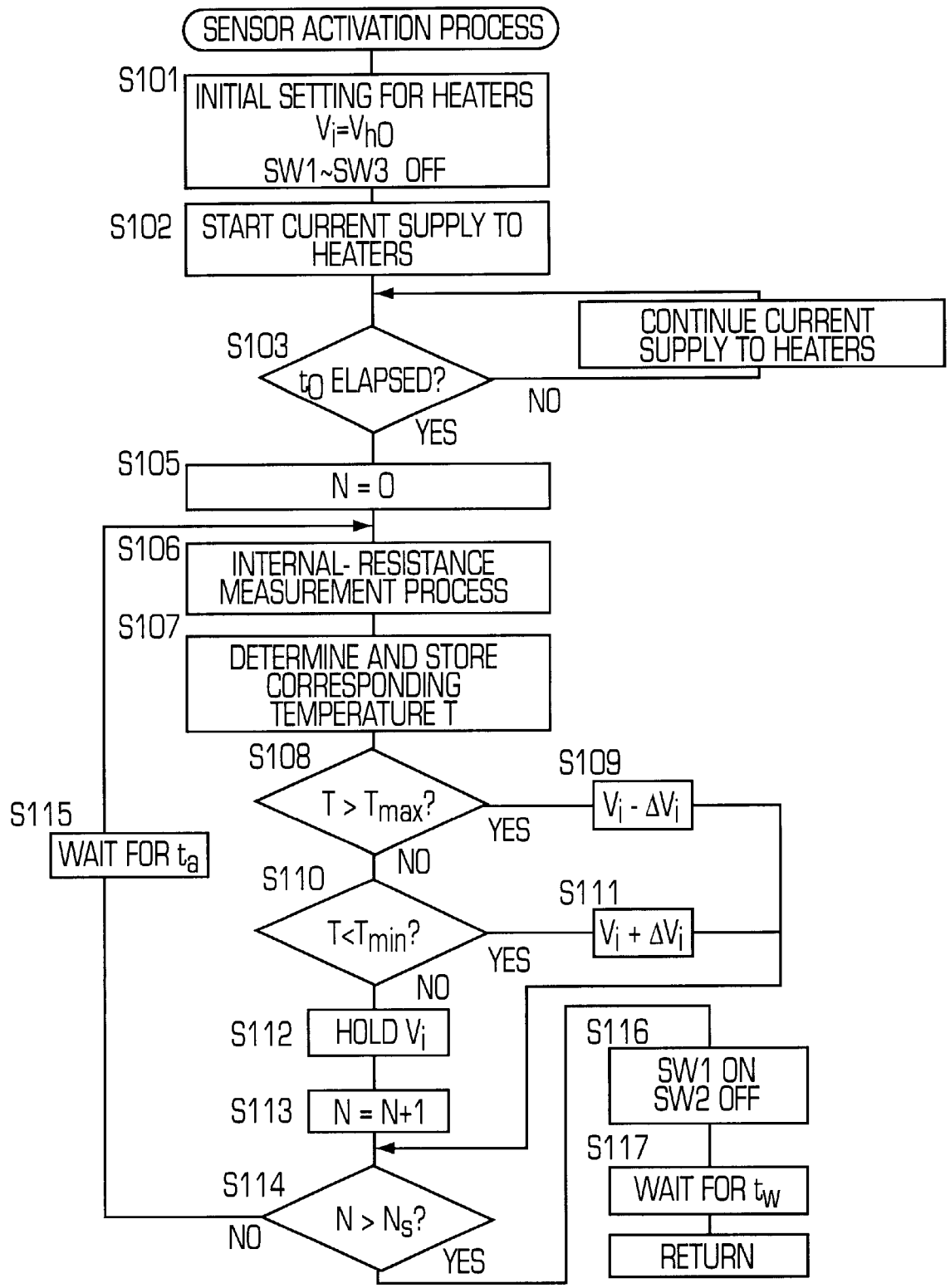
FIG. 15 is a flowchart showing the details of the sensor activation process shown in FIG. 14.
Figure 16:
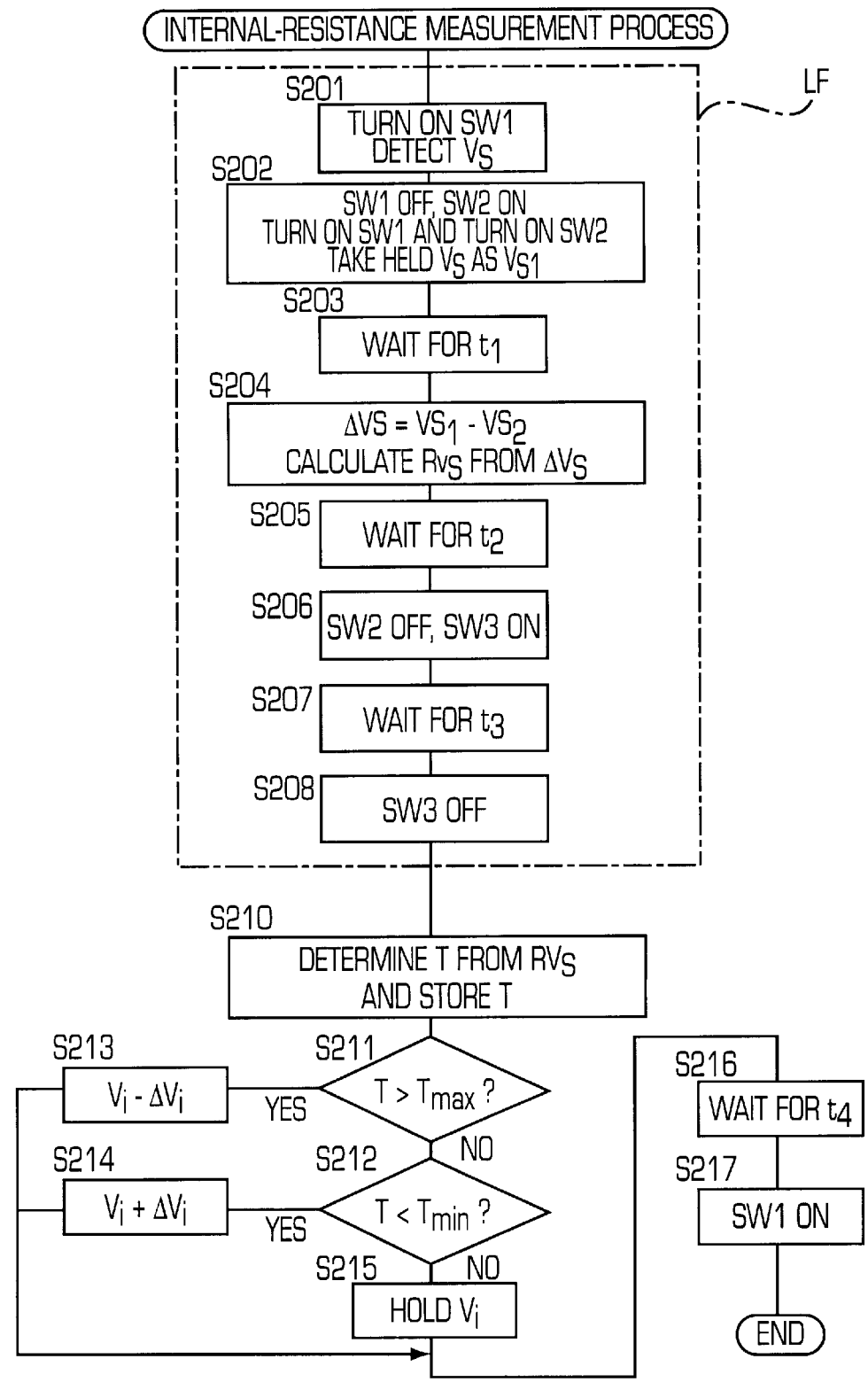
FIG. 16 is a flowchart showing the details of the internal-resistance measurement process shown in FIG. 15.

FIG. 15 shows a detailed flowchart of the sensor activation process. In step S101, a control value $V_i$ for the heater control circuit 72 is set to an initial setting value $V_{h0}$. At this time, all of the switches SW1 to SW3 of the analog switch circuit 79 are turned off. In step S102, the initial setting value $V_{h0}$ as the heater control voltage $V_i$ is output to the heater control circuit 72, thereby starting to apply current to the heaters. In step S103, upon the elapse of a predetermined time $t_0$ after the start of the application of current to the heaters, a temperature control process is initiated. In step S105, an activation judgment counter number N is cleared.

Figure 11:
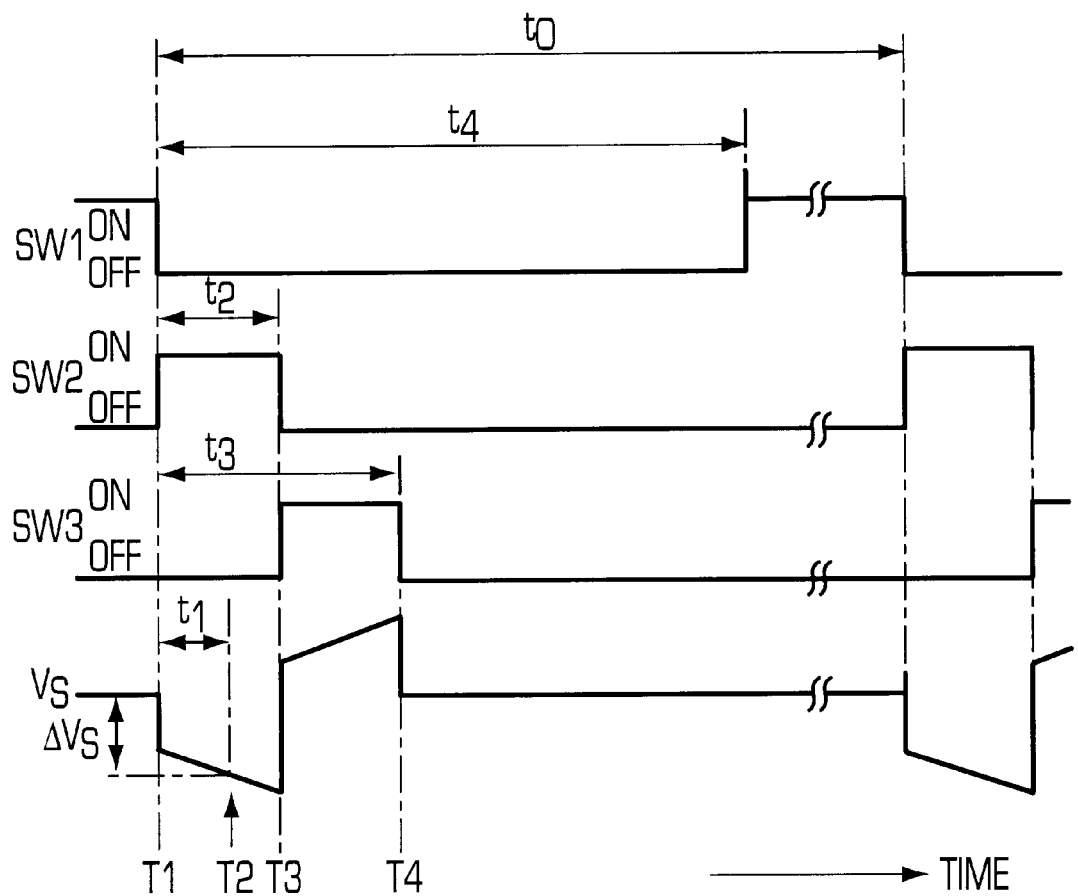
FIG. 11 is an operation timing chart of switches during measurement of the internal resistance of the oxygen concentration detection element.

Next, in step S106, an internal-resistance measurement process is initiated. The process flow will be described with reference to the flowchart of FIG. 16 (the below description covers only steps S201 to S208 represented by LF) and the circuit diagram of FIG. 10. FIG. 11 shows an operation timing chart for the switches SW1 to SW3 of the analog switch circuit 79 (FIG. 6) and variation in the voltage signal $V_S$ of the oxygen reference electrode 14 of the oxygen concentration detection element 4. In FIG. 10, the S&H circuit 120 includes a capacitor 121 for holding, when the switch SW1 of the analog switch circuit 79 turns off, the value of the output voltage $V_S$ measured immediately before the switch SW1 goes off; an operational amplifier 122 (hereinafter referred to as a "voltage follower 122") serving as a voltage follower; and an operational amplifier 123 (hereinafter referred to as a "differential amplifier 123") for amplifying the difference between the output voltage of the voltage follower 122 and the output voltage $V_S$ received directly from the oxygen reference electrode 14.

The process flow of the FIG. 16 will next be described. In step S201, the switch SW1 of the analog switch circuit 79 is turned on. As a result, the output voltage signal $V_S$ at the oxygen reference electrode 14 of the oxygen concentration detection element 4 is output to the first pump element control circuit 56 via the voltage follower 122. At this time, the terminal voltage of the capacitor 121 varies according to the level of $V_S$. In step S202, when the timing of measurement of the internal resistance is reached, the switch SW1 is turned off, and the switch SW2 is turned on. Then, the capacitor 121 holds the value of the output voltage $V_{S1}$ as measured immediately before the switch SW1 goes off. The thus-held output voltage signal $V_{S1}$ is supplied to the first pump element control circuit 56 via the voltage follower 122. Thus, the first pump element control circuit 56 continues to operate by receiving the held output voltage $V_{S1}$ even while the switch SW1 is off for measurement of the internal resistance, thereby preventing a problem such that the oxygen concentration of the first processing chamber 9 of the NOx sensor 1 varies greatly.

When the switch SW2 goes on, a constant current $I_C$ for detection of the internal resistance is applied to the oxygen concentration detection element 4. As a result, the output voltage $V_S$ of the oxygen concentration detection element 4 drops by a value corresponding to the internal resistance. The difference $\Delta V_S$ between this value of the output voltage $V_S$ and the previously held $V_{S1}$ value (i.e., an output voltage as measured before $I_C$ is applied) is amplified by the differential amplifier 123, passes through the A/D converter circuit 64, and is then input to the microprocessor 52. Taking as $V_{S2}$ the value of the output voltage $V_S$ of the oxygen concentration detection element 4 as measured after the elapse of a constant voltage $t_1$ after the application of the constant current $I_C$ is started, the output $\Delta V_S (= V_{S1} - V_{S2}$; an internal-resistance detection signal) of the differential amplifier 123 is stored in the measurements memory area of a RAM 55. The internal resistance $RV_S$ is calculated by dividing $\Delta V_S$ by the constant current $I_C$ and is then stored in the measurements memory area of the RAM 55 (S204).

The reason why $V_S$ is measured after the elapse of the predetermined time $t_1$ as measured from the start of the application of the constant current $I_C$, is as follows. When the constant current $I_C$ is applied to the oxygen concentration detection element 4, oxygen is transported within the oxygen concentration detection element 4 in a direction opposite that of the current flow. Thus, the oxygen concentration as measured at the opposite sides of the oxygen concentration detection element 4 varies. As a result, an electromotive force $E_m$ generated by a concentration cell effect varies with the continuing application of the current IC, and, as shown in FIG. 11, the value of $V_S$ varies as well. In order to secure appropriate accuracy in measuring the internal resistance, it is important that variation of $V_S$ which arises unavoidably in association with the application of the current be made substantially constant. Since the constant current $I_C$ is used for measuring the internal resistance, by exercising control such that the current application period before measurement of $V_S$ always becomes $t_1$, the amount of oxygen transported in association with the application of the current, i.e., variation in the oxygen concentration as measured at the opposite sides of the oxygen concentration detection element 4, becomes substantially constant. Accordingly, variation in the electromotive force $E_m$ generated by a concentration cell effect can be made substantially constant, and variation in $V_S$ can be made substantially constant as well.

The application of the constant current $I_C$ causes variation in the oxygen concentration as measured at the opposite sides of the oxygen concentration detection element 4. This feature raises the following problem. When the NOx sensor 1 resumes measuring the NOx concentration, the variation of oxygen concentration may affect the accuracy in measuring the NOx concentration. Also, when the internal resistance of the oxygen concentration detection element 4 is relatively high, oxygen ions have difficulty moving through the oxygen concentration detection element 4, potentially causing polarization in association with current application.

In order to solve this problem, the present embodiment employs the following method. In steps S205 to S208 of FIG. 16, after the elapse of a predetermined time $t_2$ after detection of $V_S$, the switch SW2 is turned off to terminate application of the constant current $I_C$. At the same time, the switch SW3 is turned on so that the constant-current power circuit 78 (modification current application means) having a polarity opposite that of the power circuit 77 applies correction current $I_A$ in a direction opposite that of $I_C$ for a time $t_3$, which is substantially equal to a total application time, $t_1+t_2$, of $I_C$. Subsequently, the switch SW3 is turned off (step S208). As a result, oxygen is transported within the oxygen concentration detection element 4 in an amount substantially equal to and in a direction opposite to the above-mentioned case, thereby canceling the variation of the oxygen concentration caused by the application of $I_C$. Thus, the state before measurement of the internal resistance can be substantially re-established. Notably, as in the case where the duration of the application of the current $I_C$ for measurement of the internal resistance of the oxygen concentration detection element 4 can be made sufficiently short, when the effect of the application of $I_C$ on variation in the oxygen concentration as measured at the opposite sides of the oxygen concentration detection element 4 is judged small, the constant-current power circuit 78 of FIG. 6 for generating the correction current $I_A$ can be omitted (in this case, the analog switch circuit 79 may be of a fewer number of switch channels).

In FIG. 15, as mentioned previously, a certain relationship exists between the value of $RV_S$ and an element temperature T of the oxygen concentration detection element 4. By storing this relationship as correction information in the data storage element 66 (FIG. 5), the element temperature T can be determined from the value of $RV_S$. Also, the value of $RV_S$ itself can be used as temperature information. In the present embodiment, the data storage element 66 contains a map representing the relationship between the internal resistance $RV_S$ and the element temperature T. The temperature T is obtained by reference to this map and by interpolation (step S107). A calculated value of the internal resistance $RV_S$ is stored in the RAM 55 (FIG. 5). A newly detected or calculated value of the internal resistance $RV_S$ overwrites an existing one for updating.

In steps S108 and S110, the microprocessor 52 judges whether the thus-determined element temperature T falls within the set temperature range of an upper limit $T_{max}$ and a lower limit $T_{min}$. When the element temperature T is higher than the upper limit $T_{max}$, the heater control voltage $V_i$ is decreased by a predetermined value $\Delta V_i$ so as to suppress heating performed by the heaters 2 and 8 (step S109). By contrast, when the element temperature T is lower than the lower limit $T_{min}$, the heater control voltage $V_i$ is increased by $\Delta V_i$ so as to accelerate heating performed by the heaters 2 and 8 (step S111). When the element temperature T falls within the set temperature range, i.e., $T_{min} \leq T \leq T_{max}$, the heater control voltage $V_i$ is maintained at the current value, and the activation judgment counter number N is incremented (steps S112 and S113).

The above-mentioned process of steps S106 to S113 is repeated at predetermined intervals ta until the activation judgment counter number N reaches a set value $N_S$, for example (steps S114 and S115). When the number N reaches $N_S$, judging that the element temperature T is substantially held within the above-mentioned set temperature range, the microprocessor 52 turns off the switch SW2 and turns on the switch SW1 of the analog switch circuit 79 (FIG. 6), performs warm-up for a predetermined time $t_w$ and then ends the activation process (steps S116 and S117).

Referring back to FIG. 14, upon completion of the activation process S1, the microprocessor 52 proceeds to step S2. In step S2, the microprocessor 52 detects the pump currents $I_{p1}$ and $I_{p2}$ and determines the oxygen concentration $C_{OX}$ and the NOx concentration $C_{NX}$. However, since the pump currents $I_{p1}$ and $I_{p2}$ vary with the element temperature T, the following correction is performed (step S3). First, the microprocessor 52 reads the value of the internal resistance $RV_S$ of the oxygen concentration detection element 4 stored in 5 the RAM 55 (FIG. 5) and determines the corresponding temperature T by referring to the aforementioned map 301. Notably, pump current correction values $\Delta I_{p1}$ and $\Delta I_{p2}$ for the pump currents $I_{p1}$ and $I_{p2}$, respectively, can be experimentally determined. Based on the experimental data, a map is prepared which represents the relationship between $\Delta I_{p1}$ and the element temperature T as well as the relationship between $\Delta I_{p2}$ and the element temperature T. The map is stored in the data storage section 66. The pump current correction value $\Delta I_P$ can be determined by reference to the map and by interpolation. The pump current correction values $\Delta I_{p1}$, and $\Delta I_{p2}$ are added to actually measured $I_{p1}$ and $I_{p2}$, respectively, for correction of $I_{p1}$ and $I_{p2}$. Then, the oxygen concentration $C_{OX}$ is determined from the corrected pump current $I_{p1}$, and the NOx concentration $C_{NX}$ is determined from the corrected pump currents $I_{p1}$ and $I_{p2}$ (step S4). The thus-determined values of $C_{OX}$ and NOx are output in step S5. Subsequently, processing returns to step S2, and the above-mentioned process is repeated.

After the element temperature T is set in the activation process, control of the element temperature T continues by execution of an internal-resistance measurement process similar to that described above, in parallel with the above-mentioned process for detecting the NOx concentration. This process flow is shown in FIG. 16. Notably, the CPU 53 (FIG. 5) periodically executes this process routine as an interruption process routine to the routine of FIG. 15 while counting clock pulses (generated by an unillustrated clock circuit). A cycle of executing the interruption process routine can be set to, for example, 0.3 ms to 1 ms. When the execution cycle is in excess of 1 ms, the accuracy of temperature measurement and accuracy in detecting concentration by the sensor may not be maintained at a sufficiently high degree. When the execution cycle is less than 0.3 ms, the processing time for temperature measurement accounts for an excessively large percentage of the processing time of the CPU 53, potentially failing to provide a sufficiently high degree of concentration detection accuracy. However, by employing a high-speed CPU having a high clock rate as the CPU 53, the execution cycle may be made less than 0.3 ms.

The process of steps S201 to S208 for measuring the internal resistance $RV_S$ has already been described above with respect to the sensor activation process, and thus the description of the process is not repeated. The process of steps S210 to S215 for determining the element temperature T from $RV_S$ and for determining the heater control voltage $V_i$ from the determined element temperature T is substantially similar to the sensor activation process of steps S107 to S112 in FIG. 15, and thus the description of these processes is also not repeated. In step S216, the CPU 53 waits for a time $t_4$. Then, in step S217, the CPU 53 turns on the switch SW1 and completes the internal-resistance measurement process. Subsequently, the concentration measurement process routine of FIG. 14 is executed again. A measured value of the element temperature T is updated each time the internal-resistance measurement process is performed. Information regarding the thus-updated element temperature T is used in the concentration measurement process routine of FIG. 14. The heater temperature is also periodically corrected for the measured element temperature T.

Figure 13A:
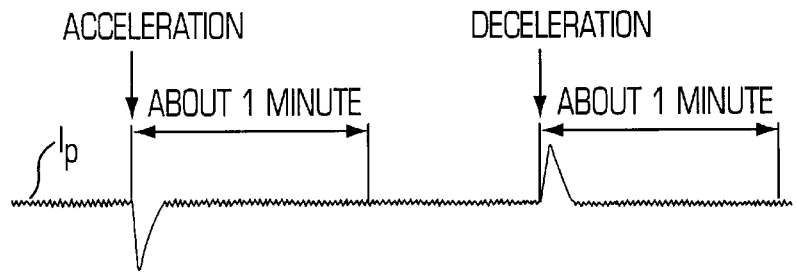
FIG. 13A is a profile showing an example measurement of variation in pump current associated with abrupt acceleration or abrupt deceleration of an engine.
Figure 13B:
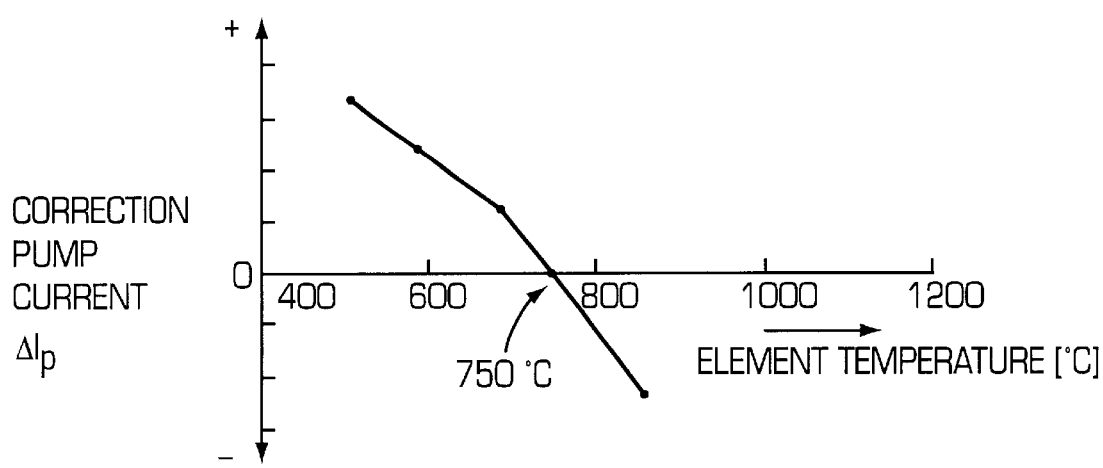
FIG. 13B is a graph showing an example relationship between the element temperature and a correction pump current.

Thus, by means of the heaters 2 and 8, the oxygen concentration detection element 4 is held at a set temperature at a high degree of accuracy, thereby improving accuracy in measuring the NOx concentration of a measurement gas. When an exhaust gas emitted from an automobile engine is the measurement gas, even when the exhaust gas temperature varies abruptly due to abrupt acceleration or deceleration of the engine as shown in FIG. 13A with a resultant abrupt variation in the temperature T of the oxygen concentration detection element 4, the measurement of the NOx concentration can be continued at a relatively high degree of accuracy without waiting for restoration of the element temperature T to a regular level. This is achieved by correction of the oxygen pump current $I_p$ for the variation of the element temperature.

Figure 17:
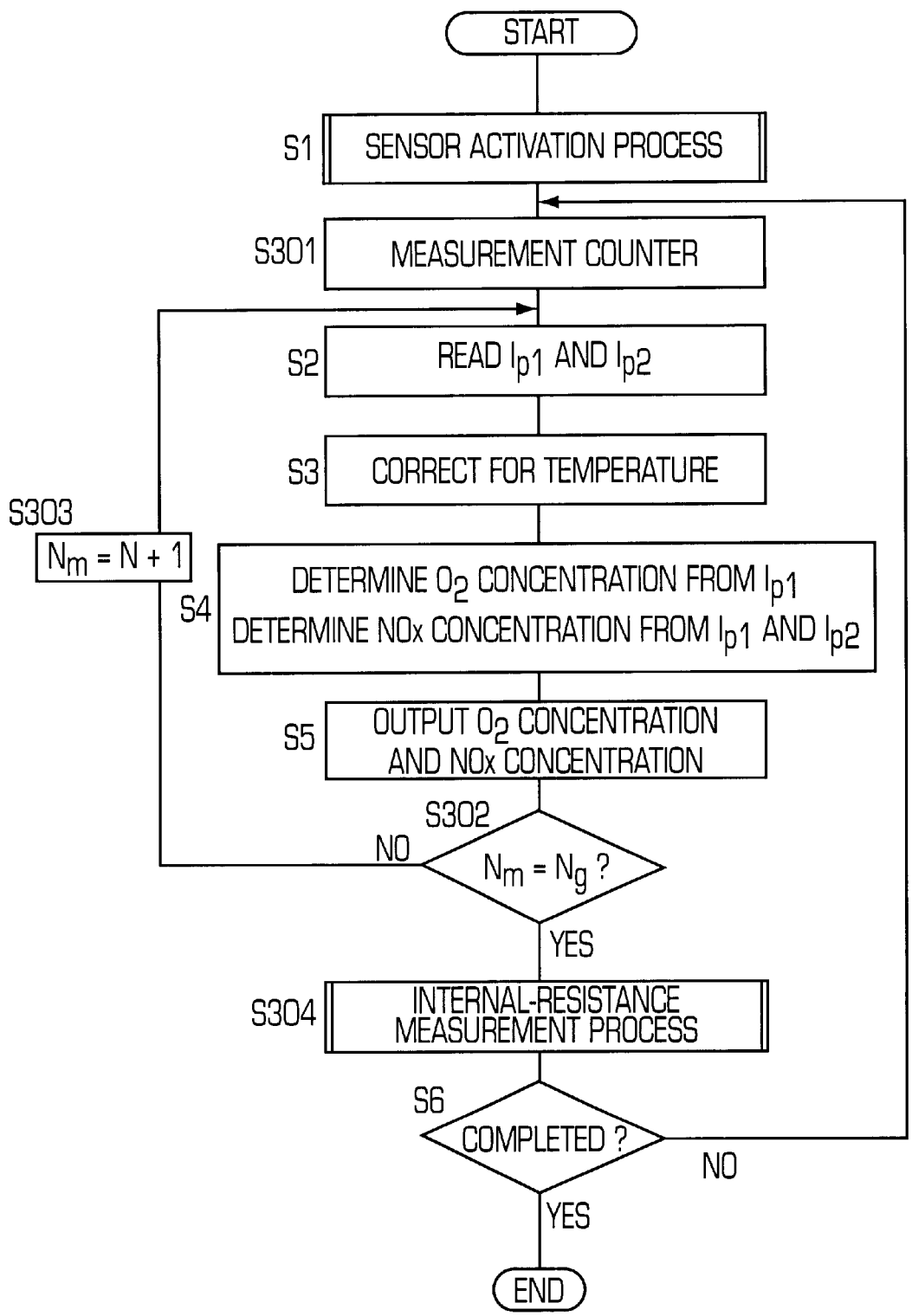
FIG. 17 is a flowchart showing another sequence of control steps performed by the microprocessor in the system of FIG. 5.

Instead of execution as an interruption routine to the concentration measurement process routine, the internal-resistance measurement process can be executed as a sub-routine of the concentration measurement process routine. This is exemplified in FIG. 17. In the flowchart of FIG. 17, the process of steps S1 to S5 for determining and outputting the $O_2$ and NOx concentrations is identical to that of FIG. 14. The process of FIG. 17 is different from that of FIG. 14 in that steps S301 to S303 are added in order to increment a measurement counter Nm each time judgment is completed. When $N_m$ reaches a predetermined count number $N_g$ in step S302, the internal-resistance measurement process identical to that of FIG. 16 is executed in step S304. After the internal-resistance measurement process is executed, processing returns to step S301, in which the measurement counter $N_m$ is reset to 1. Subsequently, the above-mentioned processes are repeated. In this method, the internal-resistance measurement process is executed periodically, but not necessarily at equal time intervals; specifically, each time the concentration measurement process is executed a predetermined number of times. This method is advantageous in that the NOx concentration or oxygen concentration measurement process is not interrupted by the internal-resistance measurement process. Thus, the frequency of error occurrence decreases.

Furthermore, in place of using two constant-current power circuits 77 and 78 as shown in FIG. 6, an unillustrated polarity switching circuit and a single constant-current power circuit may be used, and the polarity switching circuit changes over the polarity of the constant-current power circuit. Alternatively, a circuit may be employed which can generate current under instructions regarding current and polarity from the microprocessor 52 (for example, a circuit including a voltage/current conversion circuit).

Figure 21:
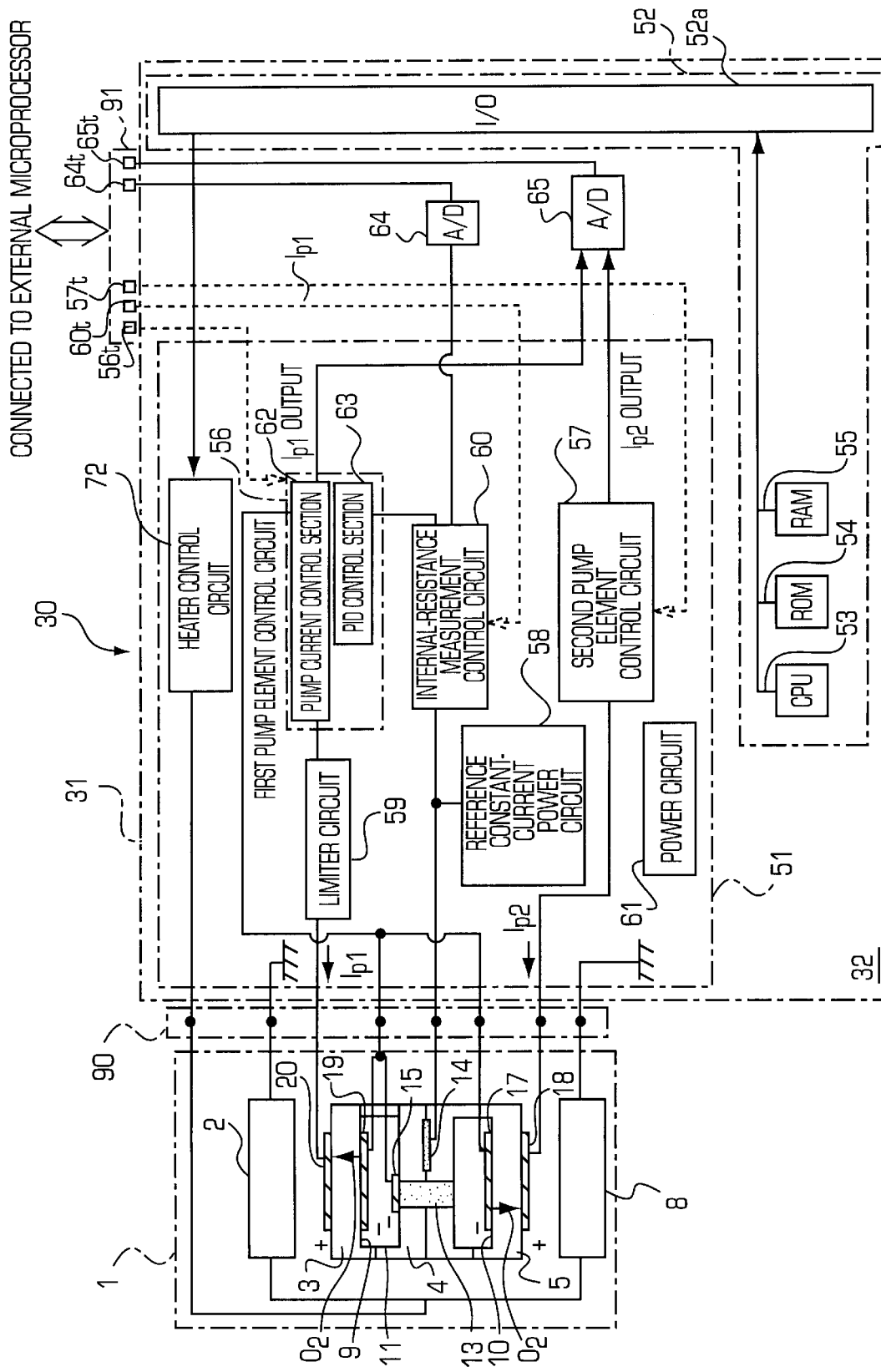
FIG. 21 is a block diagram showing a first modified example of the NOx sensor control circuit unit.
Figure 22:
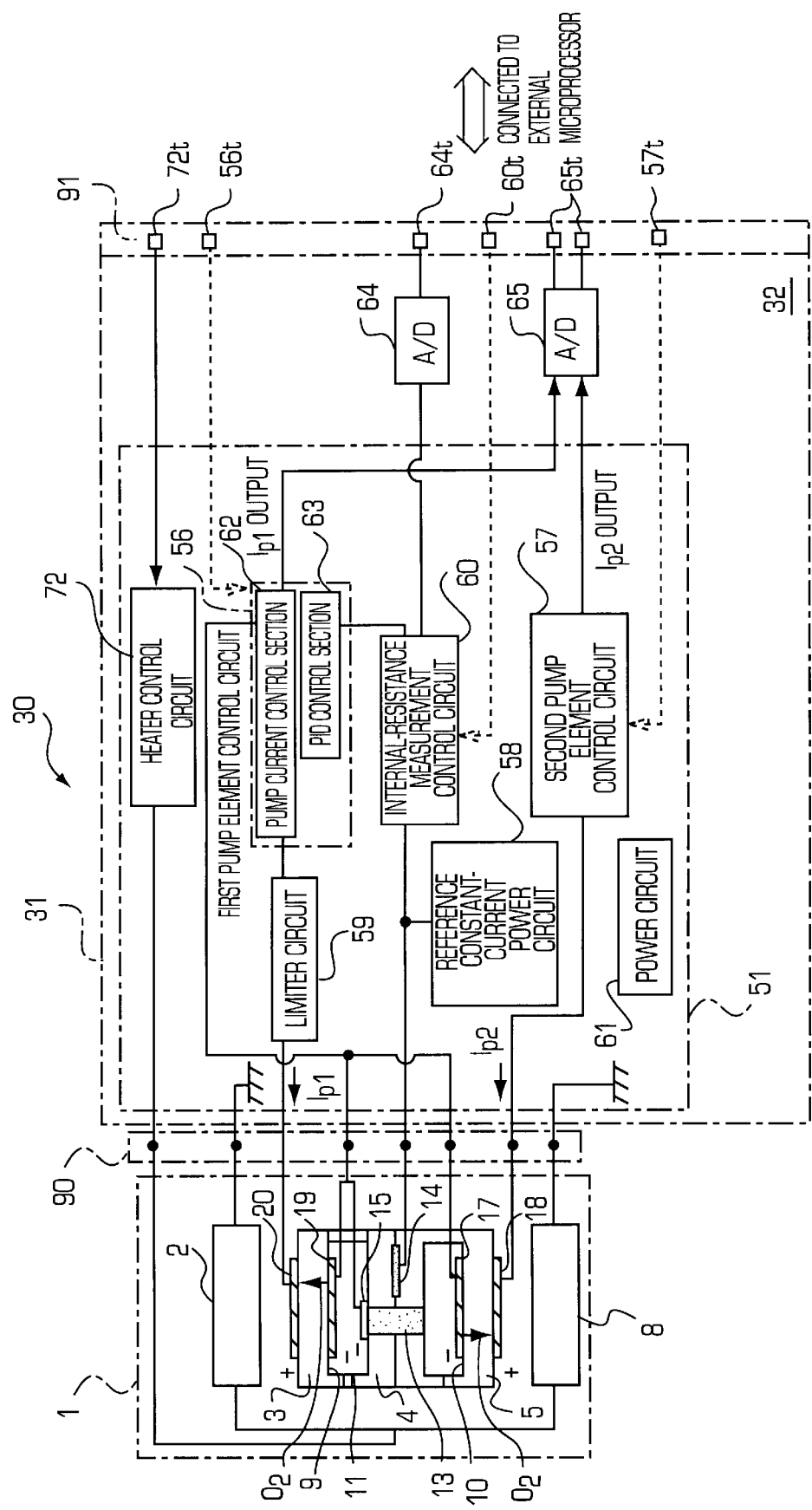
FIG. 22 is a block diagram showing a second modified example of the NOx sensor control circuit unit.

The control circuit unit 31 of FIG. 5 includes the microprocessor 52. However, as shown in FIG. 22, the microprocessor 52 may be excluded. In this case, a connector (or a card edge provided on the board 32) 91 includes an input terminal 72t to the heater control circuit 72, output terminals 64t and 65t from the A/D converter circuits 64 and 65, respectively, and control instruction signal input terminals 56t, 60t and 57t. An external microprocessor (the one mounted on an automobile, for example) is detachably connected to the connector 91. In the case of FIG. 21, the microprocessor 52 is mounted, but is adapted only to issue control instructions to the heater control circuit 72; and an external microprocessor is connected to the connector 91 which includes the output terminals 64t and 65t from the A/D converter circuits 64 and 65, respectively, and control instruction signal input terminals 56t, 60t and 57t.

Next another method for determining the oxygen concentration $C_{ox}$ from $I_{p1}$ and for determining the NOx concentration $C_{NX}$ from $I_{p1}$ and $I_{p2}$ will be described. First, a standard NOx sensor 1 of FIG. 1 is selected. By using the standard NOx sensor 1 and a test gas which does not contain oxygen and which serves as a measurement gas, the characteristic of the second pump current $I_{p2}$ relative to the NOx concentration (equivalent to an NOx concentration output characteristic as observed when the first pump current $I_{p1}$ is made substantially zero) is measured. The thus-measured $I_{p2}$ characteristic is stored in the ROM 54 (FIG. 18) of the microprocessor 52 as the standard current parameter characteristic. The microprocessor 52 detects the first pump current $I_{p1}$ and the second pump current $I_{p2}$, and determines the NOx concentration of the measurement gas from the detected values of $I_{p1}$ and $I_{p2}$ and on the basis of the standard current parameter characteristic. When the measurement gas does not contain oxygen, the second pump current $I_{p2}$ changes at a substantially constant rate with the NOx concentration. This constant rate of change is hereinafter called a gain.

Figure 18:
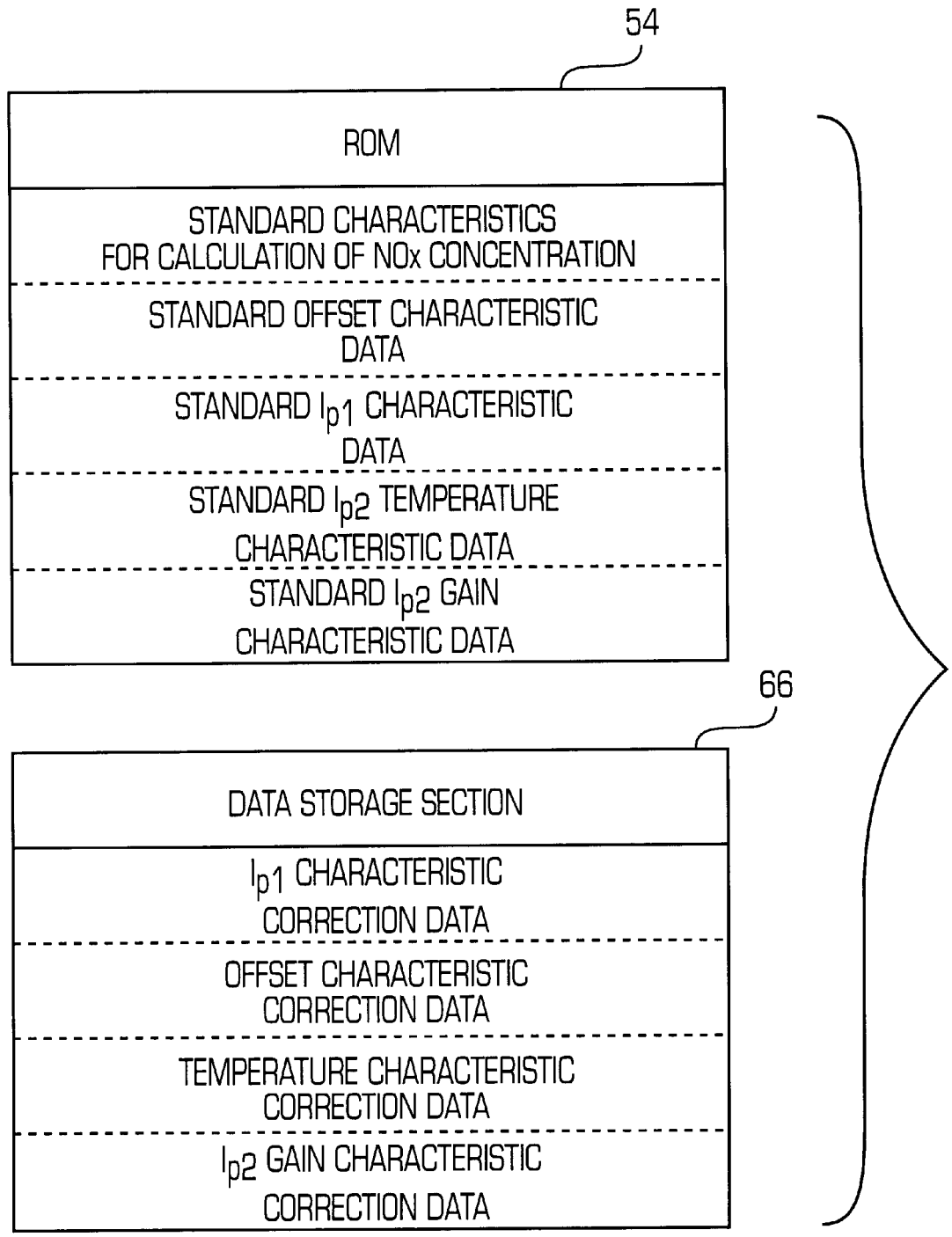
FIG. 18 includes two explanatory diagrams showing the contents of a ROM of the microprocessor and the contents of the data storage element used in a second method for determining NOx concentration.
Figure 19:
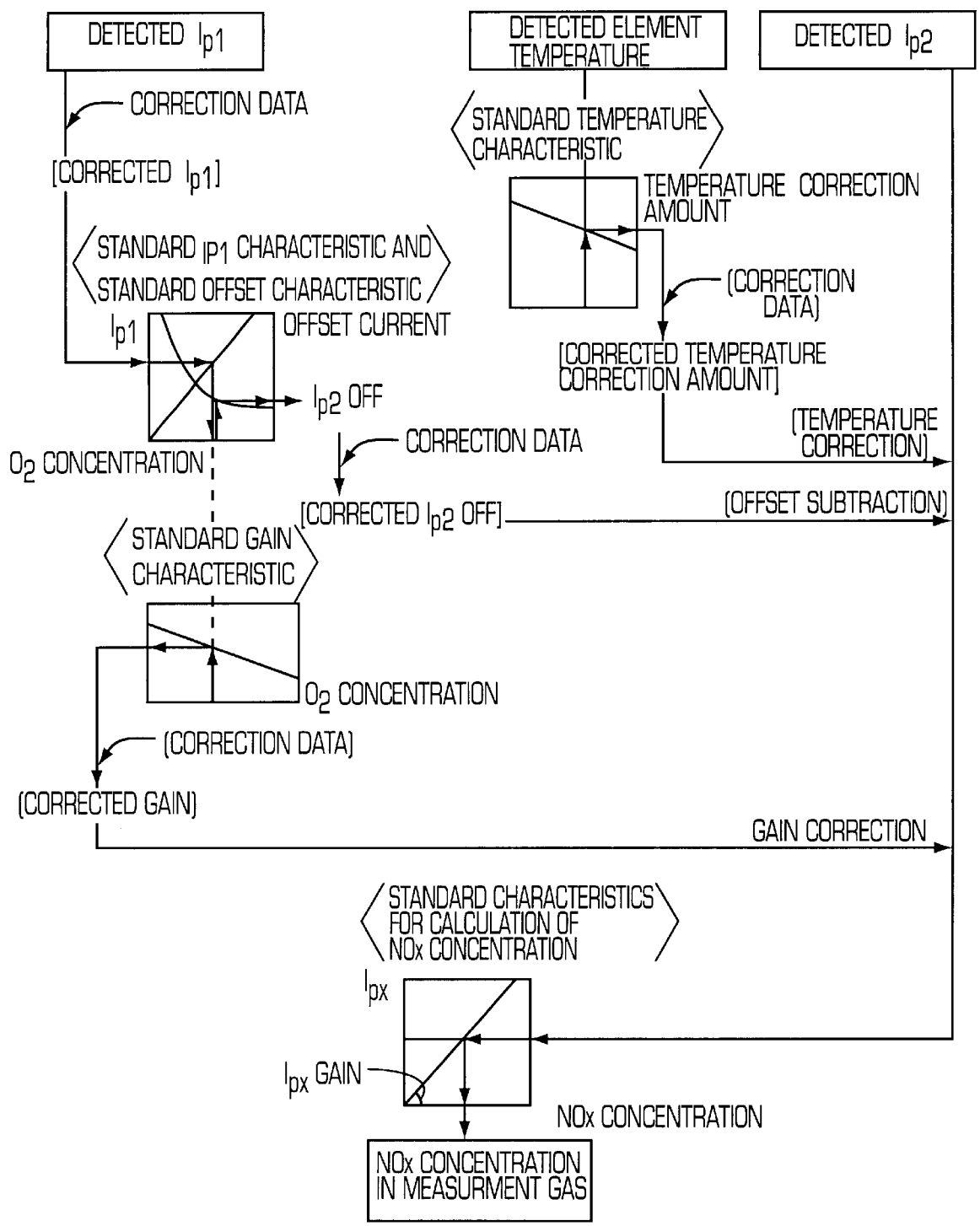
FIG. 19 is an explanatory diagram showing the procedure for determining the NOx concentration according to the above second method.

In the present embodiment, the concentration of oxygen in the first processing chamber 9 is controlled to a level of the aforementioned partial pressure range ($10^{-10}$ to $10^{-6}$ atm) so as not to excessively decompose an NOx component of the measurement gas. Thus, not only NOx contained in the measurement gas but also oxygen remaining in the first processing chamber 9 flows into the second processing chamber 10. Accordingly, the second pump current $I_{p2}$ not only varies with the NOx concentration of the measurement gas but is also influenced by the oxygen concentration of the measurement gas. That is, even when the measurement gas does not contain any NOx component, the second pump current $I_{p2}$ varies with the concentration of oxygen in the measurement gas. To compensate for this phenomenon, by using the standard NOx sensor 1 and a test gas which does not contain any NOx component as a measurement gas, the characteristic of the second pump current relative to oxygen concentration (hereinafter, this second pump current is referred to as the "offset current", and this characteristic is referred to as the "offset characteristic") is measured in advance (FIG. 19). The thus-measured offset characteristic is stored in the ROM 54 (FIG. 18) of the microprocessor 52 as the standard offset characteristic (see FIG. 19). A new current parameter $I_{px}$ is determined by subtracting an offset current $I_{p2OFF}$ corresponding to the current oxygen concentration (obtained from the first pump current $I_{p1}$) from the detected second pump current $I_{p2}$; in other words, on the basis of the second pump current $I_{p2}$ and the first pump current $I_{p1}$. Based on the new current parameter $I_{px}$ and the above-mentioned standard current parameter characteristic the NOx concentration is determined.

During pump current control, the first pump current $I_{p1}$ varies depending on the oxygen concentration of the measurement gas. To compensate for this phenomenon, by using the standard NOx sensor 1 and a test gas which does not contain any NOx component as a measurement gas, the characteristic of the first pump current relative to oxygen concentration (hereinafter referred to as the "$I_{p1}$ characteristic") is measured in advance. The thus-measured $I_{p1}$ characteristic is stored in the ROM 54 (FIG. 18) of the microprocessor 52 as the standard $I_{p1}$ characteristic (see FIG. 19). The oxygen concentration is determined from the detected first pump current $I_{p1}$ and on the basis of the standard $I_{p1}$ characteristic. The offset current $I_{p2OFF}$ is obtained from the thus-determined oxygen concentration as described above.

Because the second pump current $I_{p2}$ varies with the temperature of the NOx sensor 1 (hereinafter referred to as the "element temperature"), the detected second pump current $I_{p2}$ is preferably corrected for the element temperature. Upon an abrupt change in the temperature of the measurement gas, the temperature control fails to follow the temperature change of the measurement gas. As a result, the temperature change of the measurement gas may cause a change in the element temperature. In this case, the second pump current $I_{p2}$ varies with the element temperature. To compensate for this phenomenon, by using the standard NOx sensor 1, the characteristic of the second pump current $I_{p2}$ relative to the element temperature (hereinafter referred to as the "temperature characteristic") is measured in advance. The thus-measured temperature characteristic is stored in the ROM 54 (FIG. 18) of the microprocessor 52 as the standard temperature characteristic (see FIG. 19). Based on the standard temperature characteristic, a temperature correction amount is obtained from the element temperature which, in turn, is obtained from the internal resistance $RV_S$. By using the thus-obtained temperature correction, the detected second pump current $I_{p2}$ is corrected for temperature.

Also, when the NOx concentration is to be determined, the standard current parameter characteristic is preferably corrected in accordance with the oxygen concentration of the measurement gas because the gain varies with the oxygen concentration. In the present embodiment, by using the standard NOx sensor 1, a gain at a certain oxygen concentration (for example, zero) and a gain at another oxygen concentration are measured in advance. Based on the measured values of the gain, the linear-function-like characteristic of the gain relative to the oxygen concentration (hereinafter referred to as the "gain characteristic") is calculated. The thus-calculated gain characteristic is stored in the ROM 54 (FIG. 18) of the microprocessor 52 as the standard gain characteristic (see FIG. 19). Based on the standard gain characteristic, a gain correction amount is obtained from the oxygen concentration which, in turn, is obtained from the first pump current $I_{p1}$. By using the thus-obtained amount of correction of the gain, the detected second pump current $I_{p2}$ is corrected accordingly. The above-mentioned ROM 54 serves as standard characteristics storage means.

The above-mentioned $I_{p1}$ characteristic, offset characteristic, temperature characteristic, gain characteristic and $I_{p2}$ characteristic differ slightly among individual NOx sensors 1. Thus, if NOx concentration is determined using the above-mentioned standard characteristics, a satisfactory degree of measurement accuracy is not obtained among various NOx sensors 1. Thus, according to the present embodiment, these characteristics are previously measured for each of the NOx sensors 1, and corresponding correction data ($I_{p1}$ characteristic correction data, offset characteristic correction data temperature characteristic correction data and gain characteristic correction data) are generated such that the previously measured characteristics become equal to the above-mentioned respective standard characteristics. The thus-generated correction data are stored in the data storage element 66.

Figure 20:
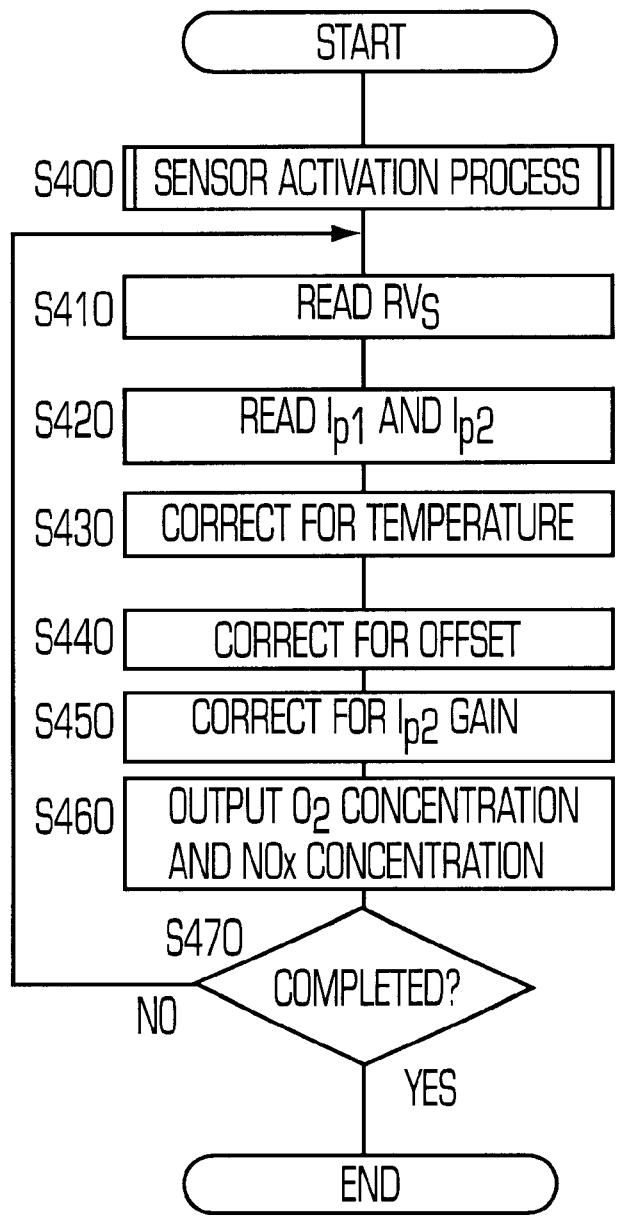
FIG. 20 is a flowchart showing a sequence of process steps according to the above second method.

The procedure for detecting the NOx concentration will next be described according to the flowchart of FIG. 20. First, in step S400, a sensor activation process is executed in a manner identical to that of FIG. 15. Upon completion of the activation process, processing proceeds to step S410, in which the internal resistance $RV_S$ of the oxygen concentration detection element 4 is read. In step S430, based on the internal resistance $RV_S$ read in step S410, a correction amount for the second pump current $I_{p2}$ is calculated, and then the second pump current $I_{p2}$ is corrected accordingly.

Specifically, in order to accurately determine the NOx concentration from the second pump current $I_{p2}$ during abrupt variations in the temperature of the measurement gas, the temperature of the oxygen concentration detection element 4, i.e., the element temperature, is obtained from the internal resistance $RV_S$ of the oxygen concentration detection element 4. A temperature correction amount corresponding to the thus-obtained element temperature is obtained on the basis of the standard temperature characteristic stored in the ROM 54 (FIG. 18). The thus-obtained temperature correction amount is corrected through use of the temperature characteristic correction data read from the data storage element 66, yielding a corrected temperature correction amount. By using the corrected temperature correction amount, the second pump current $I_{p2}$ is corrected for temperature. In the case of the standard NOx sensor 1, the corrected temperature correction amount agrees with the temperature correction amount obtained on the basis of the standard temperature characteristic.

After correcting for temperature, processing proceeds to step S440. In step S440, an offset current is subtracted from the second pump current $I_{p2}$ corrected for temperature, yielding a current parameter $I_{px}$. Specifically, the first pump current $I_{p1}$ is corrected using the $I_{p1}$ characteristic correction data read from the data storage element 66, yielding the corrected first pump current $I_{p1}$. The oxygen concentration of the measurement gas is obtained from the corrected first pump current $I_{p1}$ and by using the standard $I_{p1}$ characteristic. The offset current $I_{p2OFF}$ is obtained from the thus-obtained oxygen concentration and by using the standard offset characteristic. The thus-obtained offset current $I_{p2OFF}$ is corrected by using the offset characteristic correction data read from the data storage element 66, yielding the corrected offset current $I_{p2OFF}$. The corrected offset current $I_{p2OFF}$ is subtracted from the second pump current $I_{p2}$, yielding the current parameter $I_{px}$.

In the subsequent step S450, the current parameter $I_{px}$ is corrected for gain. Specifically, a gain is obtained from the oxygen concentration which, in turn, has been obtained from the first pump current $I_{p1}$ in step S440, and by using the standard gain characteristic. The thus-obtained gain is corrected using the gain correction data read from the data storage element 66, yielding a corrected gain. A gain correction coefficient (a gain in the corrected gain/standard current parameter characteristic, for example) is obtained from the corrected gain. By using the gain correction coefficient, the current parameter $I_{px}$ is corrected for the gain. In the case of the standard NOx sensor 1, the corrected gain agrees with the gain obtained using the standard gain characteristic.

In the subsequent step S460, the NOx concentration is obtained from the current parameter $I_{px}$ corrected for the gain and by using the standard current parameter characteristic. The thus-obtained NOx concentration is output as that of the measurement gas.

Because the above-mentioned correction data are peculiar to individual NOx sensors, each NOx sensor is provided with the data storage element 66. When the connector 90 of FIG. 8 is disconnected in order to use another NOx sensor 1 for measuring NOx concentration, the data storage element 66 that accompanies the NOx sensor 1 replaces the one that was previously used.

While the invention has been described in detail and with reference to specific embodiments thereof, it will be apparent to one skilled in the art that various changes and modifications can be made therein without departing from the spirit and scope thereof.

What is claimed is:

1. An NOx sensor control circuit unit adapted for use by connection to an NOx sensor, said NOx sensor comprising:

a first processing chamber which is an internal chamber of the NOx sensor, wherein a measurement gas containing NOx and oxygen is introduced into the first processing chamber via a first diffusion-controlling passage;

a second processing chamber which is an internal chamber of the NOx sensor, wherein a gas contained in the first processing chamber is introduced into the second processing chamber via a second diffusion-controlling passage;

an oxygen concentration detection element formed of an oxygen-ion conductive solid electrolyte sandwiched between porous electrodes and adapted to measure the oxygen concentration of gas contained in the first processing chamber, said oxygen concentration detection element having an internal resistance that varies with element temperature;

a first pump element formed on an oxygen-ion conductive solid electrolyte sandwiched between porous electrodes and adapted to pump out oxygen from the first processing chamber;

a second pump element formed of an oxygen-ion conductive solid electrolyte sandwiched between porous electrodes and adapted to pump out oxygen from the second processing chamber; and a heating element for heating the first pump element, the oxygen concentration detection element and the second pump element, said NOx sensor control circuit unit comprising:

a first pump element control circuit for controlling a voltage applied to the first pump element to thereby control the partial pressure of oxygen in the first processing chamber such that an output voltage from the oxygen concentration detection element becomes substantially constant;

a first pump current detection circuit for detecting a first pump current flowing through the first pump element and for outputting a first pump current detection signal indicative of the detected current flowing through the first pump element;

a second pump element control circuit for applying a constant voltage to the second pump element in a direction so as to pump out oxygen from the second processing chamber;

a second pump current detection circuit for detecting a second pump current flowing through the second pump element and for outputting a second pump current detection signal indicative of the detected current flowing through the second pump element;

an internal-resistance measurement control circuit for measuring the internal resistance of the oxygen concentration detection element;

a heating control circuit for controlling said heating element;

a microprocessor comprising heating control instruction means for instructing the heating control circuit to control heating performed by the heating element, based on the internal resistance of the oxygen concentration detection element as measured by the internal-resistance measurement control circuit, such that the temperature of the first pump element, the temperature of the oxygen concentration detection element and the temperature of the second pump element approach a target temperature; and oxygen concentration information generation means for determining the oxygen concentration of the measurement gas based on the first pump current detection signal and NOx concentration information generation means comprising a microprocessor including a data storage element containing a two-dimensional numeric table relating NOx concentration to the first and second pump current detection signals for determining the NOx concentration of the measurement gas based on the first and second pump current detection signals, wherein the first pump element control circuit, the first pump current detection circuit, the second pump element control circuit and the second pump current detection circuit are accommodated within a single housing.

2. The NOx sensor control circuit unit according to claim 1, further comprising an A/D converter circuit for converting into digital signals the first pump current detection signal output from said first pump current detection circuit and the second pump current detection signal output from said second pump current detection circuit.

3. The NOx sensor control circuit unit according to claim 2, wherein said microprocessor further comprises oxygen concentration information generation means for generating information regarding the oxygen concentration of the measurement gas based on the first pump current detection signal which has undergone A/D conversion by said A/D converter circuit and NOx concentration information generation means for generating information regarding the NOx concentration of the measurement gas based on the first pump current detection signal and the second pump current detection signal which have undergone A/D conversion by said A/D converter circuit.

4. The NOx sensor control circuit unit according to claim 3, wherein said microprocessor outputs digital signals, and said NOx sensor control circuit unit further comprises a D/A converter circuit for converting to an analog signal a digital signal related to at least any of the oxygen concentration information, the NOx concentration information, air-fuel ratio information generated on the basis of the oxygen concentration information, and excess-oxygen ratio information generated on the basis of the oxygen concentration information, among digital signals output from said microprocessor, and for outputting a converted analog signal.

5. The NOx sensor control circuit unit according to claim 4, further comprising a display device for displaying at least any of the oxygen concentration of the measurement gas, the NOx concentration of the measurement gas, the air-fuel ratio, and the excess-oxygen ratio on the basis of a digital signal related to at least any of the oxygen concentration information, the NOx concentration information, the air-fuel ratio information generated on the basis of the oxygen concentration information, and the excess-oxygen ratio information generated on the basis of the oxygen concentration information, among the digital signals output from said microprocessor.

6. An NOx sensor system, comprising:
an NOx sensor comprising:
a first processing chamber which is an internal chamber of the NOx sensor, wherein a measurement gas containing NOx and oxygen is introduced into the first processing chamber via a first diffusion-controlling passage;
a second processing chamber which is an internal chamber of the NOx sensor, wherein a gas contained in the first processing chamber is introduced into the second processing chamber via a second diffusion-controlling passage;
an oxygen concentration detection element formed of an oxygen-ion conductive solid electrolyte sandwiched between porous electrodes and adapted to measure the oxygen concentration of gas contained in the first processing chamber;
a first pump element formed of an oxygen-ion conductive solid electrolyte sandwiched between porous electrodes and adapted to pump out oxygen from the first processing chamber; and
a second pump element formed of an oxygen-ion conductive solid electrolyte sandwiched between porous electrodes and adapted to pump out oxygen from the second processing chamber; and
an NOx sensor control circuit unit connected to said NOx sensor comprising:
a first pump element control circuit for controlling a voltage applied to the first pump element to thereby control the partial pressure of oxygen in the first processing chamber such that an output voltage from the oxygen concentration detection element becomes substantially constant;
a first pump current detection circuit for detecting a first pump current flowing through the first pump element and for outputting a first pump current detection signal indicative of the detected current flowing through the first pump element;
a second pump element control circuit for applying a constant voltage to the second pump element in a direction so as to pump out oxygen from the second processing chamber;
a second pump current detection circuit for detecting a second pump current flowing through the second pump element and for outputting a second pump current detection signal indicative of the detected current flowing through the second pump element; and
NOx concentration information generation means for generating information regarding the NOx concentration based on the first and second pump current detection signals, wherein the first pump element control circuit, the first pump current detection circuit, the second pump element control circuit and the second pump current detection circuit are accommodated within a single housing, said NOx further comprising:
a standard characteristics information storage section for storing predetermined standard characteristics information representing correlations among the first pump current, the second pump current and the NOx concentration of the measurement gas;
a correction data storage element for storing correction data for making the previously measured characteristics of said NOx sensor equal to the standard characteristics, which characteristics represent correlations among the first pump current, the second pump current, and the NOx concentration of the measurement gas; and
a microprocessor implementing said NOx concentration information generation means,
wherein said NOx concentration information generation means detects a signal indicative of the first pump current and a signal indicative of the second pump current, corrects the detected values on the basis of the correction data, and generates information regarding the NOx concentration of the measurement gas based on the standard characteristics information.

7. An NOx sensor control circuit unit adapted for use by connection to an NOx sensor, said NOx sensor comprising:
a first processing chamber which is an internal chamber of the NOx sensor, wherein a measurement gas containing NOx and oxygen is introduced into the first processing chamber via a first diffusion-controlling passage;
a second processing chamber which is an internal chamber of the NOx sensor, wherein a gas contained in the first processing chamber is introduced into the second processing chamber via a second diffusion-controlling passage;
an oxygen concentration detection element formed of an oxygen-ion conductive solid electrolyte sandwiched between porous electrodes and adapted to measure the oxygen concentration of gas contained in the first processing chamber, said oxygen concentration detection element having an internal resistance that varies with element temperature;
a first pump element formed on an oxygen-ion conductive solid electrolyte sandwiched between porous electrodes and adapted to pump out oxygen from the first processing chamber;
a second pump element formed of an oxygen-ion conductive solid electrolyte sandwiched between porous electrodes and adapted to pump out oxygen from the second processing chamber; and
a heating element for heating the first pump element, the oxygen concentration detection element and the second pump element,
said NOx sensor control circuit unit comprising:
a first pump element control circuit for controlling a voltage applied to the first pump element to thereby control the partial pressure of oxygen in the first processing chamber such that an output voltage from the oxygen concentration detection element becomes substantially constant;
a first pump current detection circuit for detecting a first pump current flowing through the first pump element and for outputting a first pump current detection signal indicative of the detected current flowing through the first pump element;
a second pump element control circuit for applying a constant voltage to the second pump element in a direction so as to pump out oxygen from the second processing chamber;
a second pump current detection circuit for detecting a second pump current flowing through the second pump element and for outputting a second pump current detection signal indicative of the detected current flowing through the second pump element;
an internal-resistance measurement control circuit for measuring the internal resistance of the oxygen concentration detection element;

a heating control circuit for controlling said heating element; and oxygen concentration information generation means for determining the oxygen concentration of the measurement gas based on the first pump current detection signal and NOx concentration information generation means for determining the NOx concentration of the measurement gas based on the first and second pump current detection signals, said NOx sensor control circuit unit further comprising a microprocessor comprising heating control instruction means for instructing said heating control circuit to control heating performed by the heating element, based on the internal resistance of the oxygen concentration detection element as measured by the internal-resistance measurement control circuit, such that the temperature of the first pump element, the temperature of the oxygen concentration detection element and the temperature of the second pump element approach a target temperature, an A/D converter circuit for converting into digital signals the first pump current detection signal output from said first pump current detection circuit and the second pump current detection signal output from said second pump current detection circuit, wherein said microprocessor further comprises oxygen concentration information generation means for generating information regarding the oxygen concentration of the measurement gas based on the first pump current detection signal which has undergone A/D conversion by said A/D converter circuit and NOx concentration information generation means for generating information regarding the NOx concentration of the measurement gas based on the first pump current detection signal and the second pump current detection signal which have undergone A/D conversion by said A/D converter circuit, wherein said microprocessor outputs digital signals, and said NOx sensor control circuit unit further comprises a D/A converter circuit for converting to an analog signal a digital signal related to at least any of the oxygen concentration information, the NOx concentration information, air-fuel ratio information generated on the basis of the oxygen concentration information, and excess-oxygen ratio information generated on the basis of the oxygen concentration information, among digital signals output from said microprocessor, and for outputting a converted analog signal, said NOx sensor control circuit unit further comprising a display device for displaying at least two of the oxygen concentration of the measurement gas, the NOx concentration of the measurement gas, the air-fuel ratio, and excess-oxygen ratio on the basis of a digital signal related to at least any of the oxygen concentration information, the NOx concentration information, the air-fuel ratio information generated on the basis of the oxygen concentration information, and the excess-oxygen ratio information generated on the basis of the oxygen concentration information, among the digital signals output from said microprocessor.

8. The NOx sensor control circuit unit according to claim 7, comprising a display device for displaying both the oxygen concentration of the measurement gas and the NOx concentration of the measurement gas.

9. An NOx sensor control circuit unit adapted for use by connection to an NOx sensor, said NOx sensor comprising:

a first processing chamber which is an internal chamber of the NOx sensor, wherein a measurement gas containing NOx and oxygen is introduced into the first processing chamber via a first diffusion-controlling passage;

a second processing chamber which is an internal chamber of the NOx sensor, wherein a gas contained in the first processing chamber is introduced into the second processing chamber via a second diffusion-controlling passage;

an oxygen concentration detection element formed of an oxygen-ion conductive solid electrolyte sandwiched between porous electrodes and adapted to measure the oxygen concentration of gas contained in the first processing chamber;

a first pump element formed on an oxygen-ion conductive solid electrolyte sandwiched between porous electrodes and adapted to pump out oxygen from the first processing chamber;

a second pump element formed of an oxygen-ion conductive solid electrolyte sandwiched between porous electrodes and adapted to pump out oxygen from the second processing chamber; and a heating element for heating the first pump element, the oxygen concentration detection element and the second pump element, said NOx sensor control circuit unit comprising:

a first pump element control circuit for controlling a voltage applied to the first pump element to thereby control the partial pressure of oxygen in the first processing chamber such that an output voltage from the oxygen concentration detection element becomes substantially constant;

a first pump current detection circuit for detecting a first pump current flowing through the first pump element and for outputting a first pump current detection signal indicative of the detected current flowing through the first pump element;

a second pump element control circuit for applying a constant voltage to the second pump element in a direction so as to pump out oxygen from the second processing chamber;

a second pump current detection circuit for detecting a second pump current flowing through the second pump element and for outputting a second pump current detection signal indicative of the detected current flowing through the second pump element;

a heating control circuit for controlling said heating element;

oxygen concentration information generation means for determining the oxygen concentration of the measurement gas based on the first pump current detection signal and NOx concentration information generation means comprising a microprocessor including a data storage element containing a numeric expression or two-dimensional numeric table relating NOx concentration to the first and second pump current detection signals for determining the NOx concentration of the measurement gas based on the first and second pump current detection signals, wherein the first pump element control circuit, the first pump current detection circuit, the second pump element control circuit and the second pump current detection circuit are accommodated within a single housing;

an A/D converter circuit for converting into digital signals the first pump current detection signal output from said first pump current detection circuit and the second pump current detection signal output from said second pump current detection circuit; and a microprocessor comprising heating control instruction means for instructing said heating control circuit to control heating performed by the heating element such that the temperature of the first pump element, the temperature of the oxygen concentration detection element and the temperature of the second pump element approach a target temperature, wherein said microprocessor further comprises oxygen concentration information generation means for generating information regarding the oxygen concentration of the measurement gas based on the first pump current detection signal which has undergone A/D conversion by said A/D converter circuit and NOx concentration information generation means for generating information regarding the NOx concentration of the measurement gas based on the first pump current detection signal and the second pump current detection signal which have undergone A/D conversion by said A/D converter circuit, and wherein said NOx sensor further comprises a temperature detection section for detecting the temperature of at least any of the first pump element, the oxygen concentration detection element, the second pump element and the heating element, and wherein said microprocessor comprises means for performing temperature correction for information regarding the concentration of an object component selected from the group consisting of oxygen concentration information and NOx concentration information, said microprocessor generating oxygen concentration information corrected for temperature and NOx concentration information corrected for temperature on the basis of temperature detected by said temperature detection section, the first pump current detection signal and the second pump current detection signal.

10. The NOx sensor control circuit unit according to claim 9, further comprising integration means for integrating the first pump element control circuit, the first pump current detection circuit, the second pump element control circuit and the second pump current detection circuit.

11. The NOx sensor control circuit unit according to claim 9, wherein said microprocessor outputs digital signals, and said NOx sensor control circuit unit further comprises a D/A converter circuit for converting to an analog signal a digital signal related to at least any of the oxygen concentration information, the NOx concentration information, air-fuel ratio information generated on the basis of the oxygen concentration information, and excess-oxygen ratio information generated on the basis of the oxygen concentration information, among digital signals output from said microprocessor, and for outputting a converted analog signal.

12. The NOx sensor control circuit unit according to claim 11, further comprising a display device for displaying at least any of the oxygen concentration of the measurement gas, the NOx concentration of the measurement gas, the air-fuel ratio, and the excess-oxygen ratio on the basis of a digital signal related to at least any of the oxygen concentration information, the NOx concentration information, the air-fuel ratio information generated on the basis of the oxygen concentration information, and the excess-oxygen ratio information generated on the basis of the oxygen concentration information, among the digital signals output from said microprocessor.

13. The NOx sensor control circuit unit according to claim 9, wherein the oxygen concentration detection element comprises an internal resistance that varies with the element temperature to thereby serve as said temperature detection section, said NOx sensor control circuit unit further comprising an internal-resistance measurement control circuit for measuring the internal resistance of the oxygen concentration detection element.

14. The NOx sensor control circuit unit according to claim 13, wherein, on the basis of a measured internal resistance, said heating control instruction means implemented by said microprocessor instructs said heating control circuit to control heating performed by the heating element such that the first pump element, the oxygen concentration detection element and the second pump element are heated to a target temperature.

15. An NOx sensor control circuit unit according to claim 13, wherein said internal-resistance measurement control circuit comprises an internal-resistance detection current application circuit for applying a constant internal-resistance detection current to the oxygen concentration detection element.

16. The NOx sensor control circuit unit according to claim 15, wherein said microprocessor comprises internal-resistance information detection means for detecting a resistance detection voltage applied to the oxygen concentration detection element while the internal-resistance detection current is flowing through the oxygen concentration detection element as information regarding the internal resistance of the oxygen concentration detection element.

17. The NOx sensor control circuit unit according to claim 15, wherein said internal-resistance measurement control circuit further comprises a modification current application circuit for applying a modification current to the oxygen concentration detection element in a direction opposite that of the internal-resistance detection current, after applying the internal-resistance detection current to the oxygen concentration detection element so as to measure the internal resistance of the oxygen concentration detection element.

18. An NOx sensor system, comprising:
 an NOx sensor comprising:
  a first processing chamber which is an internal chamber of the NOx sensor, wherein a measurement gas containing NOx and oxygen is introduced into the first processing chamber via a first diffusion-controlling passage;
  a second processing chamber which is an internal chamber of the NOx sensor, wherein a gas contained in the first processing chamber is introduced into the second processing chamber via a second diffusion-controlling passage;
  an oxygen concentration detection element formed of an oxygen-ion conductive solid electrolyte sandwiched between porous electrodes and adapted to measure the oxygen concentration of gas contained in the first processing chamber;
  a first pump element formed of an oxygen-ion conductive solid electrolyte sandwiched between porous electrodes and adapted to pump out oxygen from the first processing chamber; and
  a second pump element formed of an oxygen-ion conductive solid electrolyte sandwiched between porous electrodes and adapted to pump out oxygen from the second processing chamber; and
 an NOx sensor control circuit unit connected to said NOx sensor comprising:
  a first pump element control circuit for controlling a voltage applied to the first pump element to thereby control the partial pressure of oxygen in the first processing chamber such that an output voltage from the oxygen concentration detection element becomes substantially constant;

a first pump current detection circuit for detecting a first pump current flowing through the first pump element and for outputting a first pump current detection signal indicative of the detected current flowing through the first pump element;

a second pump element control circuit for applying a constant voltage to the second pump element in a direction so as to pump out oxygen from the second processing chamber;

a second pump current detection circuit for detecting a second pump current flowing through the second pump element and for outputting a second pump current detection signal indicative of the detected current flowing through the second pump element;

NOx concentration information generation means comprising a microprocessor including a data storage element containing a numeric expression or two-dimensional numeric table relating NOx concentration to the first and second pump current detection signals for generating information regarding the NOx concentration based on the first and second pump current detection signals, wherein the first pump element control circuit, the first pump current detection circuit, the second pump element control circuit and the second pump current detection circuit are accommodated within a single housing;

a standard characteristics information storage section for storing predetermined standard characteristics information representing correlations among the first pump current, the second pump current and the NOx concentration of the measurement gas;

a correction data storage element for storing correction data for making the previously measured characteristics of said NOx sensor equal to the standard characteristics, which characteristics represent correlations among the first pump current, the second pump current, and the NOx concentration of the measurement gas; and a microprocessor implementing said NOx concentration information generation means, wherein said NOx concentration information generation means detects a signal indicative of the first pump current and a signal indicative of the second pump current, corrects the detected values on the basis of the correction data, and generates information regarding the NOx concentration of the measurement gas based on the standard characteristics information.

19. The NOx sensor system according to claim 18, wherein said NOx sensor further comprises a heating element for heating the first pump element, the oxygen concentration detection element and the second pump element, and said NOx sensor control circuit unit further comprises a heating control circuit for controlling said heating element.

* * * * *